United States Patent
Policastro et al.

(10) Patent No.: US 8,541,566 B2
(45) Date of Patent: Sep. 24, 2013

(54) PROMOTER INDUCIBLE BY REACTIVE OXYGEN SPECIES AND VECTOR COMPRISING THE SAME

(75) Inventors: Lucia Policastro, Buenos Aires (AR); Hebe Duran, Buenos Aires (AR); Osvaldo Podhajcer, Buenos Aires (AR)

(73) Assignees: Inis Biotech LLC, Milford, DE (US); Fundacion Instituto Leloir, Buenos Aires (AR); Comision Nacional de Energia Atomica (CNEA), Buenos Aires (AR); Consejo Nacional de Investigaciones Cientificas y Tecnicas (CONICET), Buenos Aires (AR)

( * ) Notice: Subject to any disclaimer, the term of this patent is extended or adjusted under 35 U.S.C. 154(b) by 688 days.

(21) Appl. No.: 12/597,891

(22) PCT Filed: Apr. 25, 2008

(86) PCT No.: PCT/US2008/005327
§ 371 (c)(1),
(2), (4) Date: Jun. 21, 2010

(87) PCT Pub. No.: WO2008/133971
PCT Pub. Date: Nov. 6, 2008

(65) Prior Publication Data
US 2010/0297024 A1    Nov. 25, 2010

(30) Foreign Application Priority Data
Apr. 27, 2007  (AR) ............................. P20070101837

(51) Int. Cl.
*C12N 15/00* (2006.01)
*C12N 15/67* (2006.01)
*C12N 15/86* (2006.01)

(52) U.S. Cl.
USPC ...... 536/24.1; 435/320.1; 435/69.1; 424/93.2

(58) Field of Classification Search
None
See application file for complete search history.

(56) References Cited

U.S. PATENT DOCUMENTS

| | | |
|---|---|---|
| 2006/0024780 A1 | 2/2006 | Aldaz et al. |
| 2006/0127880 A1 | 6/2006 | Harris et al. |
| 2006/0199778 A1 | 9/2006 | Ellis-Behnke et al. |
| 2008/0138330 A1 * | 6/2008 | Shie et al. ................. 424/130.1 |

FOREIGN PATENT DOCUMENTS

| | | |
|---|---|---|
| WO | WO 0196606 | * 12/2001 |
| WO | WO2006/078317 | 7/2006 |

OTHER PUBLICATIONS

Greco, et al., Novel chimeric gene promoters responsive to hypoxia and ionizing radiation. Gene Ther., 2002, vol. 9(20): 1403-11; Abstract; p. 1403, col. 1 and col. 2; p. 1404, col. 1 and col. 2; p. 1406, col. 2, p. 1407, col. 1 and col. 2; p. 1408, col. 2; and Fig. 1 and Fig. 5.

* cited by examiner

*Primary Examiner* — Maria Marvich
(74) *Attorney, Agent, or Firm* — Muncy, Geissler, Olds & Lowe, PLLC

(57) ABSTRACT

The invention provides promoters inducible by reactive oxygen species (ROS), capable of driving the expression of a gene of interest, particularly in a tumor cell. More particularly, it refers to promoters inducible by reactive oxygen species, that may be used to drive the expression of a gene of interest, such as a therapeutic gene, or a reporter gene for use in image diagnosis. The promoters comprise at least a fragment of a promoter sequence responsive to said reactive oxygen species, and corresponding to a gene highly expressed in cancer cells, wherein the fragment of the promoter sequence responsive to reactive oxygen species (ROS) is selected from the group of: the VE element of the VEGF promoter, the E6 element of the promoter of the EGR-1 gene, the MMP-1 element and a chimeric promoter containing an E6 element and a VE element. It also provides vectors carrying a human therapeutic or non therapeutic gene of interest, operably linked to said promoter sequence and compositions comprising the same.

17 Claims, 10 Drawing Sheets

Free radicals production analysis - DCFH-DA Assay

A375N tumors treated with E6(40)VE-TK with PBS (control), Dx, GCV and GCV+Dx

# PROMOTER INDUCIBLE BY REACTIVE OXYGEN SPECIES AND VECTOR COMPRISING THE SAME

FIELD OF THE INVENTION

The present invention relates to the field of gene therapy. Particularly, the present invention refers to a promoter comprising a DNA sequence capable of driving the expression of a gene of interest, particularly in a tumor cell. More particularly, the present invention refers to promoters inducible by reactive oxygen species that can be used to drive the expression of a gene of interest, such as a therapeutic gene or a reporter gene for use in image diagnosis.

BACKGROUND OF THE INVENTION

The Reactive Oxygen Species (ROS) such as the superoxide anion ($O_2^-$), the hydrogen peroxide ($H_2O_2$) and hydroxyl radical (OH), are generated as products of the normal aerobic cell metabolism. In physiological conditions there is a balance between the generation speed and the dissipation speed of the ROS. When the dissipation speed decreases or when the generation speed increases, the cell enters into a pro-oxidative or oxidative stress state. The increase of the ROS is associated with several pathologies, such as the arteriosclerosis, cardiovascular diseases, rheumatoid arthritis, neurodegenerative disorders and cancer (Valko M et al. *Free radicals and antioxidants in normal physiological functions and human disease. Int J Biochem Cell Biol* 39(1):44-84, 2007).

Several experimental evidence relate ROS with the cancer etiology for their mutagenic capacity as well as for their participation in signal transduction pathways related with the induction of the proliferation, angiogenesis, migration and metastasis (Wu W. *The signaling mechanism of ROS in tumor progression. Can Met Rev* 25:695-705, 2006). Bibliographic evidence shows that a permanent oxidative stress state may be related with the appearance of the malignant phenotype (Halliwell B. *Oxidative stress and cancer: have we moved forward? Biochem*, 402(1):1-11, 2007). It has been proved that there is a high production of $H_2O_2$ in different types of cancer, including melanoma, neuroblastoma, and breast, colon and pancreas cancer (Szatrowski, T., Nathan, C. *Production of large amounts of hydrogen peroxide by human tumor cells. Cancer Res.* 51: 794-798, 1991).

It has been proved that there is an association between the increase of the cell malignity and the increase in the production of free radicals (Policastro L., Molinari B., Larcher F., Blanco P., Podhajcer O. L., Costa C. S., Rojas P., Durán H. *Imbalance of antioxidant enzymes in tumor cells and inhibition of proliferation and malignant features by scavenging hydrogen peroxide. Mol. Carcinog.* 39(2): 103-13, 2004). In addition to this experimental evidence there are studies that show high levels of ROS in several types of cancerous tissue as compared with their normal counterparts (Toyokuni S. et al. *Persistent oxidative stress in cancer. FEBS Lett.* 358: 1-3, 1995).

Gene therapy represents a promissory therapeutic strategy, consisting on the introduction of genetic sequences in receptor cells in order to replace the defective genetic material or to confer a new cellular activity. Presently, this is one of the most important developments that are taking place in medicine. In order to modify a specific type of cell or tissue, therapeutic genes must be efficiently administered to the cell, so that the gene is expressed in the appropriate level and during a sufficient period of time. One of the most relevant requirements for the potential use of therapeutic genes in cancer—as well as in other diseases, is the selectivity of the expression of the therapeutic gene The use of gene promoters that are differentially expressed in the tumor tissue respect of the normal tissue is one of the ways of attributing that specificity. (Sadeghi H and Hitt M. *Transcriptionally targeted adenovirus vectors. Curr Gene Ther* 5(4):411-427, 2005).

However, the expression of highly expressed genes in the cancerous tissue is frequently heterogeneous among the cells of the same tumor and even more between the different tumors. A way of approaching this problem is to use promoter sequences responsive to a differential feature of the malignant environment. In this respect, some properties of the tumor micro-environment, such as hypoxia, glucose consumption, acid environments and increased angiogenesis, have been explored as distinctive features of tumors. The presence of DNA motifs responsive to these features have been studied as possible specific cancer promoters for driving the expression of therapeutic genes (Xu G. et al. *Strategies for enzyme/prodrug cancer therapy. Clin. Cancer Res.* 7: 3314-3324, 2001). For example, several works have proved that hypoxia can be used for the differential gene expression, by using elements responsive to low oxygen tension called hypoxia responsive elements (HRE, Hypoxia Responsive Elements) (Shibata T, et al. *Development of a hypoxia-responsive vector for tumor specific gene therapy. Gene Ther.* 7: 493-498, 2000). However, more recent evidence indicates that hypoxic regions are not distributed homogenously in the tumor, therefore limiting the use of HRE (Ballinger J. *Imaging hypoxia in tumor. Semin Nucl Med.* 31(4):321-9, 2001).

Recent studies describe the presence of promoter sequences sensitive to the reactive oxygen species in promoters of several genes. Among the genes that are highly expressed in cancer and that have motifs sensitive to ROS in their promoters we may mention the vascular endothelial growth factor (VEGF), the Early Growth Response-1 gene (EGR-1) and the matrix metalloproteinase promoter-1 (MMP-1). The VEGF promoter has a region GC-rich in residues that can be regulated by variations in the cellular redox state (Schafer G. et al. *Oxidative stress regulates vascular endothelial growth factorA gene transcription through Sp1 and Sp3 dependent activation of two proximal GC-rich promoter elements. JBC.* 278: 8190-98, 2003). Besides, the EGR-1 promoter has motifs rich in A and T bases that form 10 bp motifs of CC $(A/T)_6$GG bases (SEQ ID NO:29) or CArG domains (Datta R. et al. *Reactive oxygen intermediates target $CC(A/T)_6GG$ sequences to mediate activation of the early growth response 1 transcription factor gene by ionizing radiation. Proc. Natl. Acad. Sci.* 90: 2419-22, 1993). Finally, the MMP-1 promoter has a region comprised between bases −2002 and −1546 showing the response to the presence of ROS (Nelson K et al. *Elevated Sod2 activity augments matrix metalloproteinase expression: evidence for involvement of endogenous hydrogen peroxide in regulating metastasis. Clin. Cancer Res.* 9: 424-432, 2003).

US patent document 2003/0082685 to Weichselbaum et al discloses therapeutic methods for treating several types of cancer and hyperproliferative diseases, comprising the expression of a therapeutic gene driven by the EGR-1 promoter. It indicates that the therapeutic method comprises exposing the cell to ionizing radiation, inducing the EGR-1 promoter that therefore drives the expression of the genes under its control.

U.S. Pat. No. 5,830,880 to Sedlacek et al discloses a DNA construct for the prophylaxis or therapy of tumor diseases comprising an activator sequence, a cycle-regulated cell promoter module, and a DNA sequence codifying for an antitumor substance, such as an angiogenesis inhibitor, a cytostatic agent or an enzyme. A complete VEGF promoter is used, evaluating the response to hypoxia environments (low oxygen tension) of HRE motifs comprised in the VEGF promoter. The HRE motifs do not co-localize with the ROS-RE motifs.

The use of specific promoters is essential but not sufficient for a gene therapy to be effective, since it also requires for the definition of an effective therapeutic gene. One of the attractive modalities of gene therapy in cancer is the use of the suicide genes. The system basis consists of introducing an enzyme codifying gene capable of metabolizing a non-toxic pro-drug, converting the same in toxic. One of the genes mostly used is the herpes virus thymidine kinase or HSV-TK (Herpes Simples Virus thymidine kinase) that codifies for an enzyme capable of phosphorilating to the pro-drug acyclovir/ganciclovir (widely used antiviral in viral infections), an analogue to guanosine. The phosphorylated antiherpetic is incorporated to the DNA molecule, avoiding its duplication and causing cellular death (Mooften F. L., *Drug sensitivity ("suicide")genes for selective cancer chemotherapy, Cancer Gene Ther,* 1:279-287, 1994). Neighboring tumor cells that have not incorporated the gene can also be eliminated by the called bystander effect, which allows for the toxic metabolites to transfer from an affected to an unaffected cell.

Koshikawa et al (Cancer Res. 60: 2936-2941, 2000) disclose the use of the complete VEGF promoter, comprising the HRE site, which when exposed to hypoxia conditions drives the HSV-TK expression in lung carcinoma cells, where its use increases the tumor regression. The HRE motifs do not co-localize with the ROS-RE motifs.

US patent application 2001/0006954 to Weichselbaum et al discloses a DNA molecule comprising an alfa tumor necrosis factor gene (and other therapeutic genes as cytokines, toxins, tumor suppressors, etc.,) under the transcriptional control of the CArG domains of the EGR-1 promoter that are inducible by ionizing radiation.

ABSTRACT OF THE INVENTION

The present invention provides a promoter inducible by reactive oxygen species (ROS) capable of driving the expression of a gene of interest, where said promoter includes at least a fragment of a promoter sequence responsive to said reactive oxygen species and corresponding to a gene highly expressed in cancer cells.

According to a preferred embodiment of the present invention, the fragment of the promoter sequence responding to reactive oxygen species (ROS) is selected from the group of: the VE element consisting of the region −86 to −50 of the VEGF promoter (SEQ ID NO. 1), the E6 element found in the region proximal to the EGR-1 gene promoter (SEQ. ID. NO. 2), the MMP-1 element consisting of the region −2000 to −1546 of the MMP-1 promoter (SEQ ID NO. 3) and a chimeric promoter containing an E6 element spaced from a VE element by a spacing sequence.

According to an embodiment, the chimeric promoter of the present invention contains an E6 element spaced from a VE element by a sequence of between about 6 and about 200 base pairs. Preferably, the spacing sequence is of 6 base pairs, 20 base pairs, preferably 40 base pairs.

In a preferred embodiment of the invention, the chimeric promoter contains the E6 element spaced at a distance of 40 base pairs from the VE element. Said promoter is the chimeric promoter 5'E6(40)VE3' (SEQ ID NO. 12).

Also, the present invention provides a vector comprising a promoter inducible by reactive oxygen species (ROS) which includes at least a fragment of a promoter sequence responsive to said reactive oxygen species and corresponding to a gene highly expressed in cancer cells, which is operably linked to a gene of interest whose expression is desired.

In an embodiment of the invention, the vector comprises a fragment of a promoter sequence responsive to oxygen reactive species selected from the group of: the VE element consisting of the region −86 to −50 of the VEGF promoter (SEQ ID NO. 1), the E6 element is found in the region proximal to the EGR-1 gene promoter (SEQ ID NO. 2), the MMP-1 element consisting of the region −2000 to −1546 of the MMP-1 promoter (SEQ ID NO. 3) and a chimeric promoter containing an E6 element spaced from a VE element by a spacing sequence.

According to an embodiment, the vector of the present invention comprises the chimeric promoter containing an E6 element spaced from a VE element by a sequence of between about 6 and about 200 base pairs.

Even more preferably, the chimeric promoter of the present invention contains an E6 element spaced from a VE element, where the orientation of the E6 element respect of the VE element is 5'E6-VE3'.

Preferably, the spacer sequence is of 6 base pairs, 20 base pairs, more preferably 40 base pairs.

In a preferred embodiment of the invention, the vector comprises the chimeric promoter containing the E6 element spaced at a distance of 40 base pairs respect of the VE element, where said promoter is the chimeric promoter 5'E6(40) VE3' (SEQ ID NO. 12).

The vector of the present invention may be of viral or non-viral origin and contains preferably the chimeric promoter 5'E6(40)VE3' operably linked to a gene of interest, said gene being therapeutic or non therapeutic.

In another aspect of the invention, the vector may be used in gene therapy, particularly for the treatment of human diseases with high activity of free radicals, such as cancer and arthritis, among others.

The vector of the present invention can also be used in the diagnosis, for example for image monitoring of gene expression in regions of high activity levels of ROS. Particularly, the vector can be used in monitoring by bioluminescence for detecting the presence of a tumor. It is widely documented that the neovascularization plays a preponderant role in the metastasic growth, invasion and dispersion of solid tumors, and that antiangiogenic drugs could potentially be used as anticancer therapies. By using genes expressing proteins generating fluorescence or bioluminescence, whose activity is regulated by the promoters of the present invention, particularly the VE element or the chimeric promoter 5'E6(40)VE3', it is possible to diagnose and follow the presence of tumors in tissues, through optical image systems in vivo detecting the emission of light, generating two dimensional images. Among the proteins that may be used to generate bioluminescence or fluorescence we can mention: green fluorescent protein (GFP), red fluorescent protein (RFP), luciferin (LUC), etc.

In even another aspect of the invention, said vector may be included inside a cell that may be used as vehicle.

The invention also comprises the use of the elements VE, E6, MMP-1 or chimeric promoter containing an E6 element spaced from a VE element by a sequence of between about 6 and about 200 base pairs, alone or associated to other sequences, for driving the activity of any therapeutic or non therapeutic human gene, as well as their use in gene therapy and diagnosis methods.

More preferably, the invention comprises the use of VE and 5'E6(40)VE3' elements, alone or associated with other sequences, for driving the activity of any therapeutic or non therapeutic human gene, as well as its use in gene therapy and in diagnosis methods.

Additionally, the present invention provides a pharmaceutical composition comprising the vector according to the invention, in a pharmaceutically acceptable carrier.

DETAILED DESCRIPTION OF THE INVENTION

Figure 1:
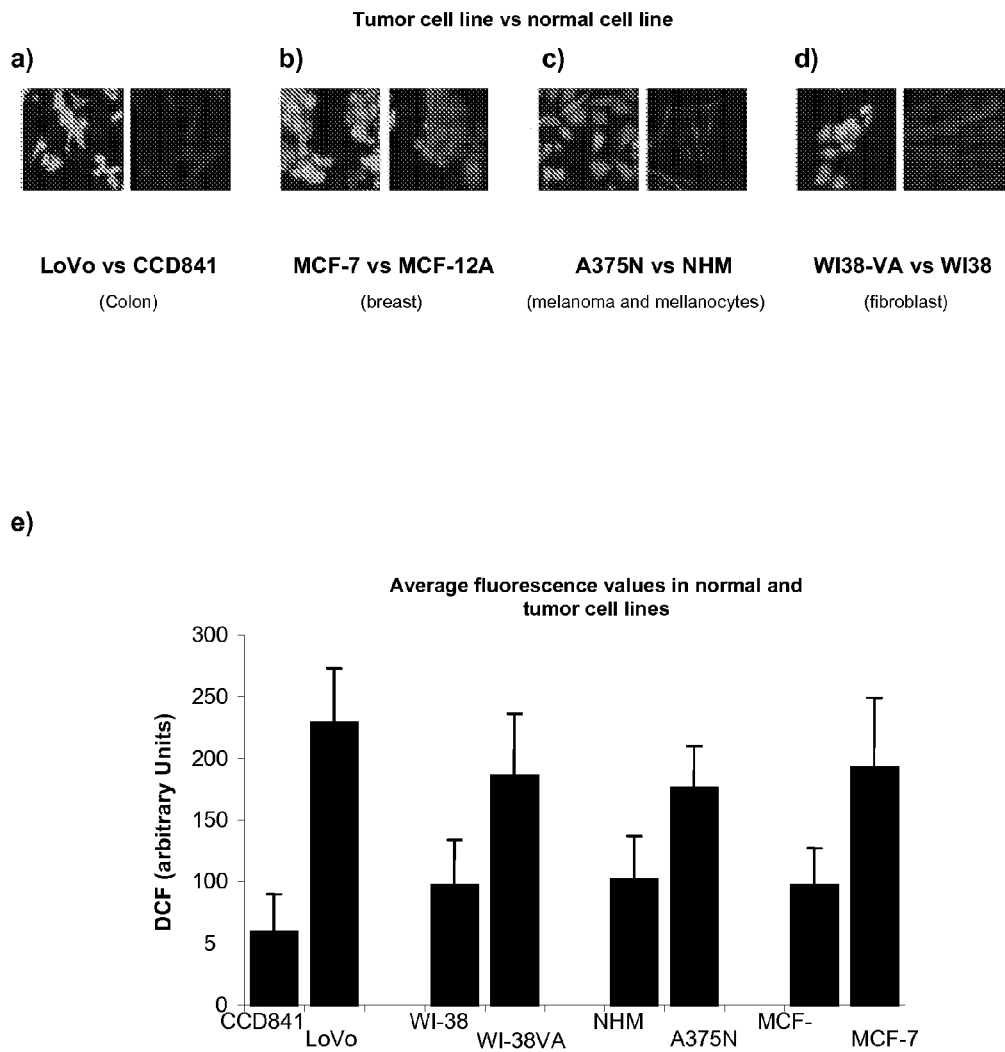
FIG. 1 shows the Images in vivo taken with confocal microscope of tumor cell lines vs their corresponding normal counterparts incubated with DCFH-DA: (a) LoVo vs CCD841 (colon), (b) MCF-7 y MCF-12A (breast), (c) A375N vs NHM (normal human melanocyte culture), (d) WI38-VA vs WI38 (fibroblasts). In (e) the average values of the fluorescence in different cell lines (arbitrary units) are shown.

According to the present invention, the vector constructs containing the different promoter sequences and the sequence of the desired therapeutic gene were made through standard ligation and restriction techniques. The DNA cleavages in the specific site were made through adequate restriction enzyme treatment, following the conditions indicated by the supplier, during approximately 3-16 hours. In general, the results of the restriction were verified through agarose gel electrophoretic separation (0.8-2%) in TAE solution (40 mM of triacetate, 2 mM $Na_2EDTA.2H_2O$ pH 8.5) using ethidium bromide and visualized with UV light in a transilluminator (Ultraviolet Products Inc., Upland, Calif.). Ligations were made through DNA bacteriophagous ligase T4, following the supplier's protocols (New England Biolab Inc., Beverly, Mass.). Relations insert:vector from 1:1 to 5:1 were used.

As used herein, "spacer sequence" refers to a DNA sequence not carrying any structural or codifying information for any of the gene functions known in the eukaryotic cells, such as for example, structural information for recognition of transcription factor or information for the codification of amino acids. However, a spacer sequence such as that used in the present invention, artificially placed inside the context of a functional gene sequence may improve the transcriptional activity of the same.

The length selection of the spacer sequence is made from the knowledge that each DNA torsion is of approximately 10 base pairs, preferably in multiples of 10 spacer sequences. The regulation of the gene expression requires the interaction of different transcription factors in the promoter regions. The efficient coupling of the different transcription factors depends on the optimal spacing between the interacting proteins. This distance depends on each case in particular, and may range between 20-200 bp (Eukaryotic transcriptional regulatory complexes: cooperativity from near and afar, Ogata K Curr Opin in Structural Biology 13:4048, 2003). In some cases, this distance may be very precise and in other cases, very flexible (18-50 bp) (Flexible promoter architecture requirements for coactivator recruitment, Chiang D et al BMC Molecular Biology, 7:16 2006).

In general, such as it is used in the present application, a "therapeutic gene" refers to a DNA sequence codifying for an amino acid or protein sequence, capable of exerting a therapeutic effect on the host cells. Preferably, according to an embodiment of the present invention, the host cells are tumor tissue cells or cells affected by other human diseases with high activity of free radicals, as arthritis, for example. Tumor cells are particularly melanoma cells, breast cells, colon cells, cervix cells, neuroblastomas.

The introduction of the vector comprising the promoter of the present invention in the host cells can be made through any construct and includes plasmids, DNA virus such as adenovirus, retrovirus, lentivirus, as well as isolated nucleotide molecules. Transference through liposomes can also be used.

The constructs or vectors of the present invention may be administered to a patient requiring the same, through an injection, by oral or topical administration, conveyed in an adequate carrier. Adequate types of carriers may be aqueous, lipid, liposomal, etc.

A two-tailed Student's t-test were used to compare two sets of data. One-way ANOVA was used to compare three or more sets of data. Tukey's or Sheffe tests were used as post hoc tests. Welch test and Games-Howells as post hoc tests were used when variances were heterogeneous. When parametric test were not possible to apply we used Kruskal-Wallis test with Man Whitney as post hoc test. A P value lower than 0.05 was considered significant.

This invention is illustrated below through detailed experimental examples. The aim of said examples is to provide an improved understanding of the invention, and they should not be considered as limiting in any way the scope of the invention, which is established in the attached claims.

EXAMPLES

Example 1

Evaluation of the Reactive Oxygen Species Production in Human Normal and Tumor Lines The production levels of the reactive oxygen species were evaluated comparatively in tumor and normal cell lines. A DCFH-DA (2',7'-dichloro-dihydrofluoresceine diacetate, Molecular Probes) assay was used, which allows to evaluate the ROS intracellular levels. The DCFH-DA spreads through the cell membrane, once internalized becomes to the plasmatic membrane due to the fact that it is metabolized by the intracellular esterases that remove the diacetate group. At the presence of ROS, the DCFH is oxidated to DCF (dichlorofluoresceine) that can be detected through the emission of fluorescence at 525 nm when excited at 488 nm.

The previous experimental evidence linking the increase of ROS in cancer are confirmed, through the comparative evaluation of the ROS production in human tumor cell lines and normal cell lines.

For this, the following comparative pairs were evaluated:
a) LoVo cell line (colon cancer, ATCC N° CCL-229) and CCD-841 (normal colon, ATCC N° CRL-1790).
b) MCF-7 tumor cell line (breast cancer, ATCC N° HTB-22) and MCF-12 A cell line (normal breast, ATCC N° CRL-10782).
c) WI38-VA cell line (transformed fetal lung fibroblasts, ATCC N° CCL-75.1) and WI38 cell line (normal fetal lung fibroblasts, ATCC N° CCL-75).
d) A375N melanoma tumor cell line and primary culture of melanocytes of human foreskin (NMH). Both provided by Dr. Estela Medrano (Houston, Tex.).

Cells were seeded in a slide in 35 cm diameter plates, after 24 hours they were incubated with 20 µM DCFH-DA (Sigma-Aldrich) during 15 minutes at 37° C. and were then washed twice with PBS. The slides were placed in a container with PBS and pictures were taken of at least 50 cells at random with confocal microscope (488 nm excitement and 515-545 nm emission). The experiment was repeated independently at least twice for each cell line.

FIGS. 1 (*a*) to (*d*) show the ROS production in the aforementioned cell lines, compared according to their tissue origin. A greater production of $H_2O_2$ was seen in cancerous lines as compared to normal lines.

FIG. 1 (*e*) represents average values of approximately 50 cells of each cell line, where it can be seen that tumor lines have ROS production levels 2 to 5 times greater than normal lines.

Example 2

Obtaining Promoter Sequences Responsive to Reactive Oxygen Species (ROS)

The promoter sequences that previously showed a response to reactive oxygen species (ROS) were chosen. 3 sequences responsive to ROS and that also belonged to gene promoters highly expressed in cancer cells were chosen. The sequences chosen were: region −86 to −50 of VEGF, referred to in the present as VE element (SEQ ID NO. 1); a motif found in the region proximal to the EGR-1 gene promoter, referred to in the present as E6 element (SEQ ID NO. 2); and the region −2000 to −1546 of the MMP-1 promoter, referred to in the present as MMP-1 element (SEQ ID NO. 3).

The VE element has three GC-rich sequences regions and previously showed a response to exogenous $H_2O_2$ in stomach cancer cells (Schafer G. et al. *Oxidative stress regulates vascular endothelial growth factorA gene transcription through Sp 1 and Sp3 dependent activation of two proximal GC-rich promoter elements. JBC.* 278: 8190-98, 2003). This element was obtained through hybridization of the following complementary synthetic oligonucleotides:

(SEQ ID NO. 4)
5'CGGGGCGGGCCGGGGGCGGGCGGGGTCCGGCGGGCGGAGA3'
and

-continued

```
                                                (SEQ ID NO. 5)
5'CGCGTCTCCGCCCCGCCGGGACCCCGCCCCCGGCCCGCCCCGGTAC3'.
```

The E6 element corresponds to 6 repetitions of a motif rich in A and T bases (CCATATAAGG) (SEQ ID NO:29) called CArG that is found in the EGR-1 gene promoter and that was obtained through hybridization of the following synthetic oligonucleotides:

```
                                                (SEQ ID NO. 6)
5'CGCGTCCATATAAGGCCATATAAGGCCATATAAGGCCATATAAGGCCA
TATAAGGCCATATAAGGC3'
and
                                                (SEQ ID NO. 7)
5'TCGAGCCTTATATGGCCTTATATGGCCTTATATGGCCTTATATGGCCT
TATATGGCCTTATATGGA3.
```

The E6 element not only responds to reactive oxygen species but also to gamma type ionizing radiation (Datta R. et al. *Reactive oxygen intermediates target CC(A/T)6GG sequences to mediate activation of the early growth response 1 transcription factor gene by ionizing radiation. Proc. Natl. Acad. Sci.* 90:2419-22, 1993) and neutron rays (Greco O et al. *Gene therapy vectors containing CArG elements from the Egr1 gene are activated by neutron irradiation, cisplatin and doxorubicin. Cancer Gene Ther.* 12(7):655-62, 2005). In both cases, the complementary oligonucleotides are flanked by cleavage sites for the restriction enzymes MluI and XhoI and were hybridized through the mixture of 0.05 nmoles of each in a final volume of 10 µl, at 55° C. during 5 minutes, gradually cooling at room temperature.

The MMP-1 element was obtained through the Polimerase Chain Reaction technique (PCR) from a genomic DNA obtained from the T47-D cell line. The following specific primers were used:

```
                                                (SEQ ID NO. 8)
5'CGGGGTACCACAGTGTATGAGACTCTTCCAGGG3'
and
                                                (SEQ ID NO. 9)
5'CGACGCGTCACTTTCCTCCCCTCCCCTTATGGATTCCTG3'.
```

In this case, the oligonucletides are flanked by the restriction sites MluI and XhoI. The PCR-amplified fragment was cloned in the first instance in the TOPO-CR4 vector (Invitrogen Corp., Carlsbad, Calif.).

Example 3

Cloning of ROS Response Elements and Confirmation of Response to $H_2O_2$

Hybridization products of complementary synthetic oligonucleotides VE and E6 and the product of PCR MMP-1, previously cloned in the TOPO-CR4 vector, were cloned independently in the sites MluI and XhoI of pmCMV vector. This vector was obtained from a modification of pGL3-basic vector (Promega Corp., Madison, Wis., USA) through the addition of a minimum promoter sequence proceeding from the CMV promoter (from citomegalovirus) containing a transcription starting site and a TATA box in the restriction sites XhoI and HindIII. The pmCMV plasmid contains the modified Firefly luciferase reporter gene (Photinus pyralis, luc+). The presence of the luciferase reporter gene allowed to quantify the basal promoter activity and the response to exogenous $H_2O_2$. The different plasmids obtained were transfected jointly with the pRL-CMV plasmid. The pRL-CMV plasmid contains the coelenterate Renilla luciferase reporter gene (Renilla reniformis) under the strong promoter CMV.

Figure 2:
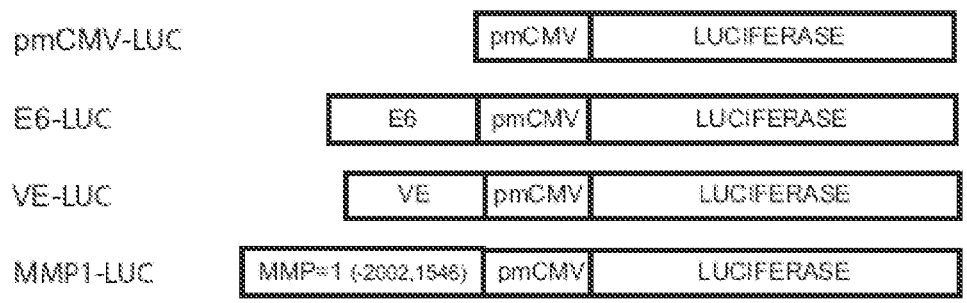
FIG. 2 shows: (a) Schematic representation of different plasmid constructs containing a single motif or promoter sequence (b) the luciferase activity of the cells transfected by the several plasmid constructs and treated with $H_2O_2$ generated by the glucose/glucose oxidase (G/GO) system; as specificity control, the cells were treated with catalase (500 U/ml). The white bars correspond to A375N melanoma cells and the black bars correspond to colorectal LoVo cancer cells. (*P<0.001, the lines over the bars show the groups that were compared; #P<0.0001, corresponds to the basal activity of VE, vs. the basal activity of E6 or MMP-1; ## P<0.0001, corresponds to VE activity in the presence of G/GO vs. the activity of E6 and MMP-1 under the same conditions).
Figure 2B:
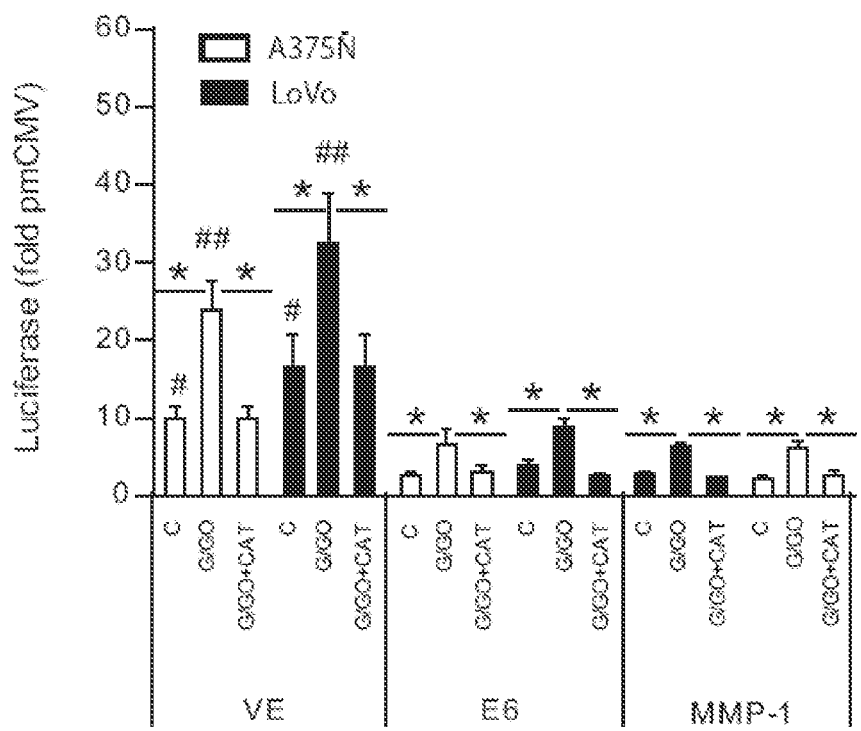

The plasmid constructs obtained, whose diagrams are shown in FIG. 2 (*a*), are as follows:
a—VE-LUC: contains a copy of the VEGF promoter region. (SEQ ID NO.1)
b—E6-LUC: contains 6 copies of the CArG sequence (SEQ ID NO. 2)
c—MMP-1-LUC: contains the −2002 to −1546 region of the MMP-1 promoter (SEQ ID NO:3).

All cloning were verified by restriction profiles and through the automatic sequencing of the vectors with universal primers P3 (CTAGCAAAATAGGCTGTCCCC) (SEQ ID NO. 24) and P2 (CTTTATGTTTTTGGCGTCTTCCA) (SEQ ID NO. 25).

The assays were made in two cell lines, A375N line (melanoma) and LoVo (colon cancer).

The cells were seeded in 24-well plates at a density of $5 \times 10^5$ cells/well. After 24 hours, the cells were transfected using Lipofectamine2000 (Invitrogen Corp., Carlsbad, Calif.) according to the conditions set by the supplier. Each well was transfected with the mixture of 0.8 µg of the plasmids obtained (VE-LUC, E6-LUC or MMP-1-LUC) with 0.1 µg of pRL-CMV plasmid. The mentioned mixture was simultaneously incubated with 1 µl Lipofectamine2000 in 50 µl of DMEM media without antibiotic during 5 minutes at room temperature. These two preparations were mixed and incubated during 20 minutes at room temperature. Serum-containing media from the cells, it was washed with PBS and it was added with 200 µl of high glucose DMEM without serum nor antibiotics; afterwards, 100 µl of means containing the lipofection mixture were added, and after 4 hours, 800 µl of culture media corresponding to each cell line were added, supplemented with SFB. The transfected cells were kept for 24 hours in a stove at 37° C. with 5% $CO_2$. The dual Luciferase Reporter Assay System (Promega Corp., Madison, Wis.) kit was used for the luciferase assay. This system evaluates the luciferase Firefly and Renilla activity in a single sequential assay thus allowing to normalize the activity measures according to the different transfection levels (Sherf, B. A y col., *Dual Luciferase Reporter Assay: An Advanced Co-Reporter Technology Integrating Firefly and Renilla Luciferase Assays. Promega Notes Magazine:* 2-9, 1996). The normalization of the data was made calculating the Relative Luciferase Units (RLU), these being defined as Firefly Luciferase Units/Renilla Luciferase Units.

The data are expressed as induction amount relative to the activity obtained with the plasmid control pmCMV (containing only the minimum promoter). The luciferase activity of the transfected cells by the different plasmid constructs and treated with $H_2O_2$ generated by the glucose/glucose oxidase (G/GO) system is shown in FIG. 2 (*b*). As a specificity control, the cells were treated with catalase (500 U/ml). The white bars correspond to A375N melanoma cells and the black bars correspond to LoVo colorectal cancer cells.

The VE element showed the highest basal transcriptional activity and induction with $H_2O_2$. The MMP-1 and E6 elements showed lesser activity regarding that of VE but similar between them. The inductions obtained through the use of the glucose/glucose oxidase system was specific of $H_2O_2$, since this was blocked in the presence of exogenous catalase (Sigma-Aldrich, 500 U/well). Besides the VE element, we selected the E6 element in order to prepare chimeric promoters with a better transcriptional response capacity and induction by $H_2O_2$. The E6 element has the advantage of being 10 times smaller in size than MMP1 and also, it has been proven to respond to ionizing radiation.

Example 4

Obtaining the Chimeric Promoters and Evaluation of the Response to $H_2O_2$

Different chimeric promoters having the E6 and VE elements placed in different relative positions respect of the transcription starting point were built. This way, the following vectors were obtained: E6(6)VE-LUC (SEQ ID NO. 10), VE(6)E6-LUC (SEQ ID NO. 11) and E6(40)VE-LUC (SEQ ID NO. 12).

Vector E6(6)VE-LUC (SEQ ID NO. 10) was obtained through the cloning of E6 element (SEQ ID NO. 2) in vector VE-LUC (SEQ ID NO. 1) and vector VE(6)E6-LUC (SEQ ID NO. 11) was obtained through the cloning of VE element (SEQ ID NO. 1) in vector E6-LUC (SEQ ID NO. 2). In both cases, complementary synthetic oligonucleotides of the sequence E6 (SEQ ID NO. 13 y 14) and from the sequence VE (SEQ ID NO. 15 y 16) were obtained, but in this case the elements were flanked by restriction sites Kpnl and Mlul. In both cases, the complementary oligonucleotides were hybridized with the mixture of 0.05 nmoles of each one in a final volume of 10 µl, at 55° C. per 5 minutes and cooling gradually up to reach room temperature. Later, the hybridized oligonucleotides E6 (SEQ ID NO. 13 and 14) and VE (SEQ ID NO. 15 and 16) were isolated and purified through agarose gel electrophoretic runs at 2% and cloned at the Kpnl and Mlul sites of the plasmids VE-LUC (SEQ ID NO. 1) and E6-LUC (SEQ ID NO. 2), respectively. The plasmid E6(40)VE-LUC (SEQ ID NO. 12) was obtained through the cloning of a spacing sequence obtained through the hybridization of the oligonucleotides: S1 of sequence: 5'CGCGTACCTCTTAG-TACATATGAATCGATGCTAGTAGCAAA3' (SEQ ID NO. 17) and S2 of sequence: 5' CGCGTTTGCTAGCATCGAT-TCATATGTACTAGTA 3' (SEQ ID NO. 18) in the Mlul site of the plasmid E6(6)VE-LUC (SEQ ID NO. 10). All clones were verified by restriction profiles and by the sequencing of the vectors with universal primers P3 (CTAGCAAAATAG-GCTGTCCCC) (SEQ ID NO. 24) and P2 (CTTTAT-GTTTTTGGCGTCTTCCA) (SEQ ID NO. 25).

The following plasmids were obtained:
a) E6(6)VE-LUC: contains the E6 element spaced at a distance of 6 base pairs respect of VE (SEQ ID NO. 10)
b) VE(6)E6-LUC: contains the VE element spaced at a distance of 6 base pairs respect of E6 (SEQ ID NO. 11).
c) E6(40)VE-LUC: contains the E6 element spaced at a distance of 40 base pairs respect of VE (SEQ ID NO. 12).

Figure 3:
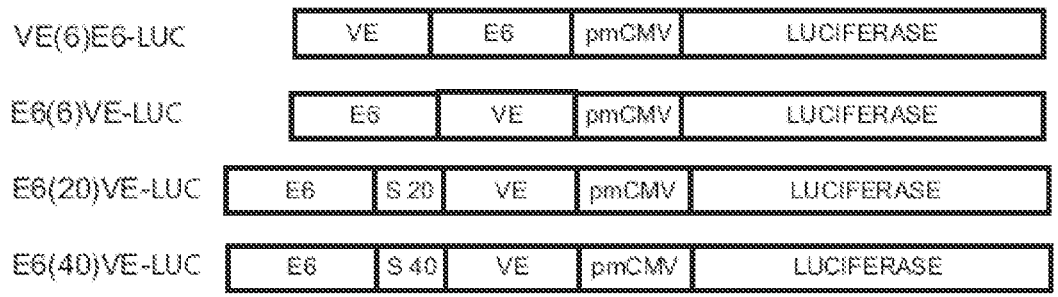
FIG. 3 shows: (a) Schematic representations of the different chimeric constructs. The terms "S20" and "S40" mean that DNA spacers of 20 or 40 bp, respectively, were included. (b) the luciferase activity of the cells transfected by the different chimeric plasmid constructs and treated with $H_2O_2$ generated by the glucose/glucose oxidase (G/GO) system; as specificity control, the cells were treated with catalase (500 U/ml); the white bars correspond to A375N melanoma cells and the black bars correspond to colorectal LoVo cancer cells. (*P<0.001 the lines over the bars show the groups that were compared; #P<0.0001, corresponds to the basal activity of E6(40)VE vs. VE; ## P<0.0001, corresponds to the E6(40) VE activity in the presence of G/GO vs. VE under the same conditions. Data are expressed as means±SD values of 3-7 independent experiments)
Figure 3:
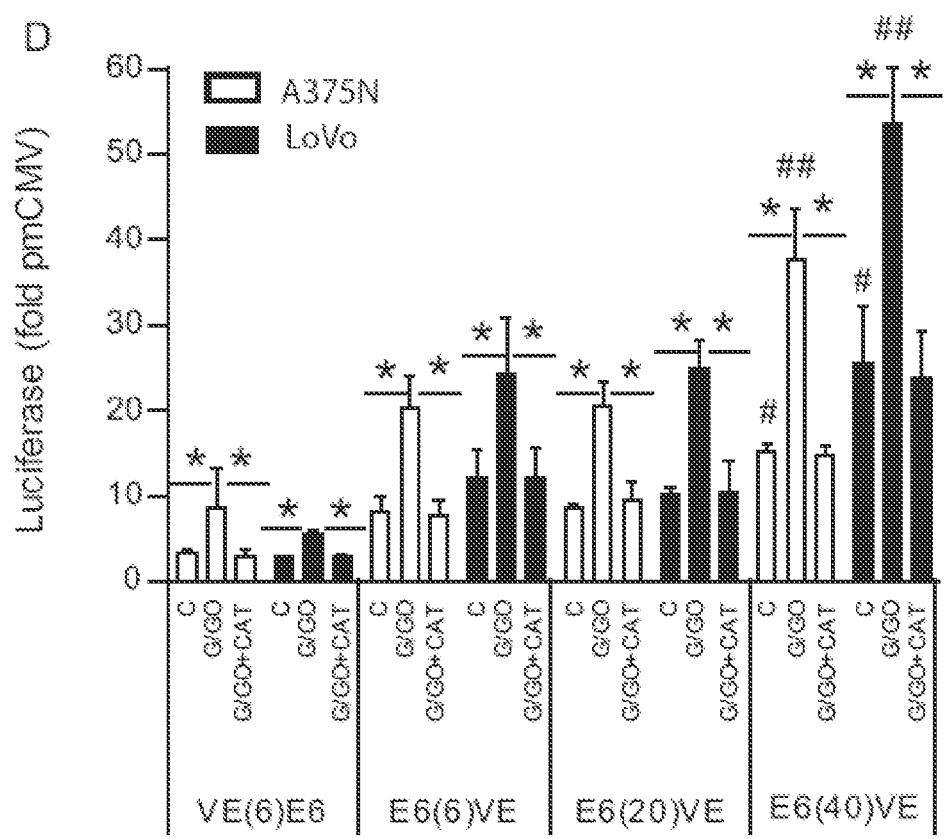

The previously mentioned plasmid constructs a, b and c were shown schematically in FIG. 3 (a).

In order to evaluate the activity of the chimeric promoters obtained, activity assays were performed and basal activity and induction with $H_2O_2$ respect to the VE-LUC vector (SEQ ID NO. 1) was compared. These experiments were made in the same way as detailed in Example 3, using the A375N (melanoma) and LoVo (colon cancer) lines. As specificity control, the cells were treated with catalase (500 U/ml). The results are shown in FIG. 3 (b) where the white bars correspond to A375N melanoma cells and the black bars correspond to LoVo colorectal cancer cells.

As can be seen in FIG. 3 (b), the E6(6)VE-LUC (SEQ ID NO. 10) and VE(6)E6-LUC (SEQ ID NO. 11) plasmids showed less activity than the vector VE-LUC (SEQ ID NO. 1) which may be due to a possible interference between the transcription factors that are linked to those elements; for that reason the selected construct is that where the E6 and VE elements are spaced by a 40 bp region. This plasmid referred to as E6(40)VE-LUC (SEQ ID NO. 12) showed a higher activity than VE-LUC (SEQ ID NO. 1), the basal activity being the addition of the activity of VE and E6. The induction specificity was supported through treatment with exogenous catalase, showing a total blockage of the promoter induction.

Example 5

Characterization of the Chimeric Promoter 5'E6(40)VE3' Response to Endogenous Variations of $H_2O_2$ Once the chimeric promoter 5'E6(40)VE3' was chosen for showing the best basal activity and for being inducible with $H_2O_2$, evaluation was made of its ability to respond to endogenous cellular variations in the ROS levels. To achieve this, several experimental models were used, i.e., increasing or decreasing the endogenous levels of the reactive oxygen species.

Figure 4:
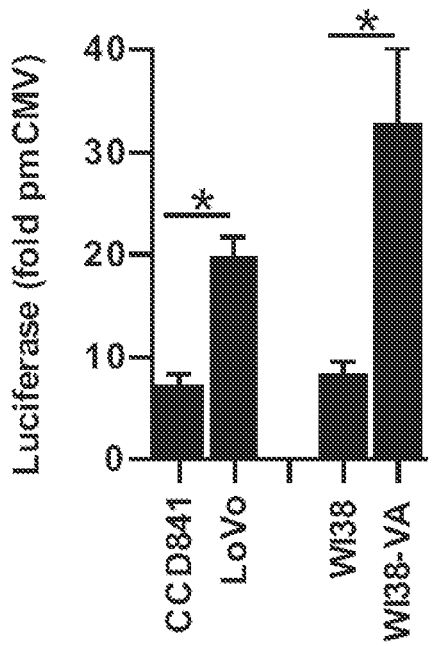
FIG. 4 shows: (a) Luciferase activity of normal (WI38, CCD-841) and malignant, or transformed, cells (LoVo and W138-VA). Data show the mean±SD of three independent experiments (*P<0.001) (b) ROS levels in F10 and G9 cells as assessed by DCF followed by FACS analysis. Data show a representative result from three independent experiments. (c) Luciferase activity in clones F10 and G9; (d) Luciferase activity in A375N and LoVo cells co-transfected with E6(40) VE-LUC and pcDNA3 or p-Cat. Cells were or not either exposed to G/GO. Luciferase activity was expressed as a-fold induction over control cells. Data show the mean±SD values of 3 independent experiments (*P<0.01).
Figure 4:
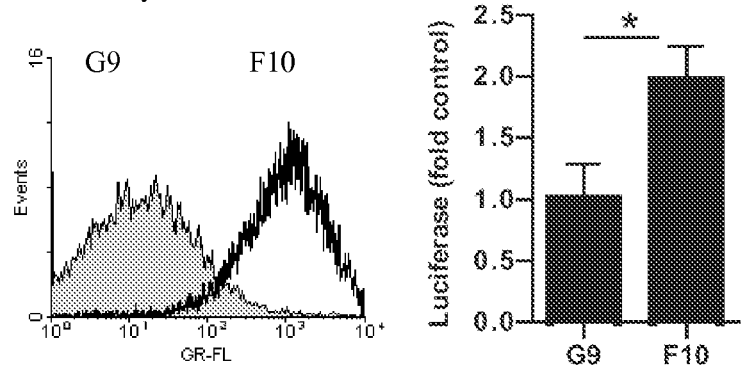
Figure 4:
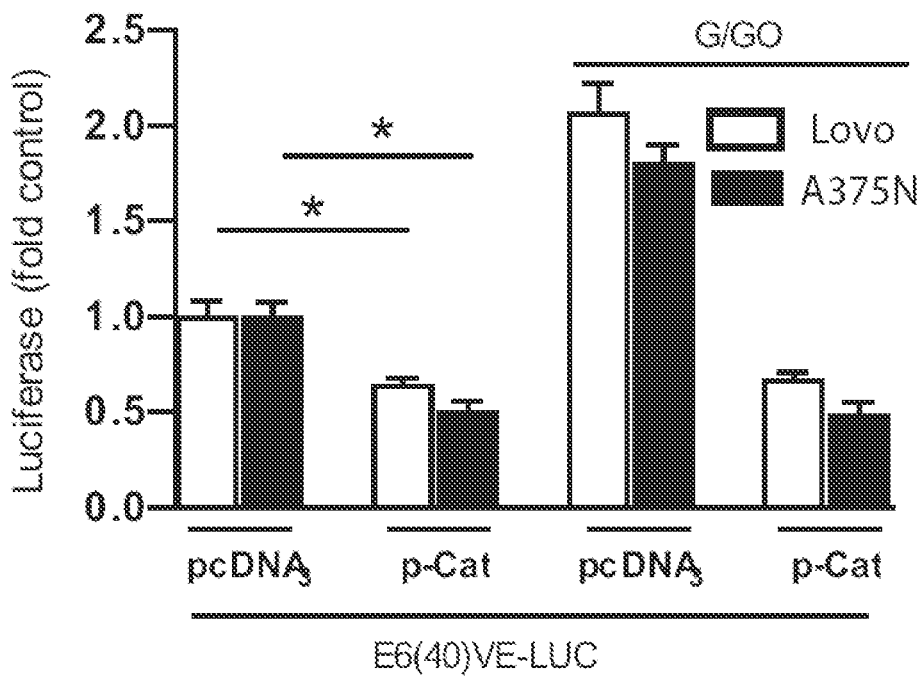

The models chosen were some of the comparative pairs of normal and tumor cell lines described in Example 1. Particularly, the comparative pairs used were: for colon, the pair CCD-841, LoVo and for fibroblasts, the pair WI38, WI38-VA. These lines were transfected with the E6(40)VE-LUC plasmid, and the results were expressed regarding the activity of pmCMV (luciferase activity). In both cases, the E6(40)VE-LUC (SEQ ID NO. 12) activity was greater in tumor lines respect of the normal lines, as shown in FIG. 4 (a).

Similarly, a cell model having high endogenous production of free radicals was generated. In order to achieve this, a plasmid containing the complementary DNA of human CuZnSOD (SEQ ID NO. 19) was stably transfected. This was amplified through the PCR technique using specific primers (SEQ ID NO. 20 and 21). The PCR product was cloned in the pcDNA6 vector which is resistant to blasticidin. The LoVo cells were stably transfected with the vector obtained and clones were selected through blasticidin (10 µg/ml) treatments during 20 days. The production of free radicals was evaluated through the assay of DCFH-DA by a Flow Cytometry analysis detecting fluorescence (FACS, Fluorescence Analyzer Cell Sorter) of 15 isolated clones. 10000 cells per sample were analyzed and at least two assays were made per each clone, and the clone F10 was selected for having highest production of $H_2O_2$ (see FIG. 4 (b-1)).

Separately, control cells were prepared by transfection of the pcDNA6 empty plasmid and, a cell population was selected with blasticidin and named G9 cells. As can be seen in FIG. 4 (b-2), the activity of E6(40)VE-LUC was 2.5 times greater in clone F10 than the activity levels reached in G9.

Finally, the endogenous levels of $H_2O_2$ were lowered through the cotransfection of a plasmid containing the human catalase cDNA (SEQ ID NO. 22). The cDNA was cloned in the vector pcDNA3 obtaining the vector pcDNA3-CAT. Cotransfection experiments were made in cell lines A375N and LoVo, simultaneously transfecting the pcDNA3-CAT plasmid (1 µg/well) and the vector E6(40)VE-LUC (1 µg/well). Also, control cells were prepared by transfection with the pcDNA3 plasmid (empty) and with the vector E6(40) VE-LUC. In both cases, 0.1 µg/renilla was also transfected in order to normalize the data to the transfection levels in each case. The results, shown in FIG. 4 (c), were relative to the activity levels of the cells transfected with pcDNA3 and the vector E6(40)VE-LUC, taking this level of activity as 1.

LoVo and A375N cells were transfected. In both cases, the activity of E6(40)VE-LUC lowered 50% when it was cotransfected with the pcDNA3-CAT plasmid (see FIG. 4 (c)), making evident that part of the basal activity of 5'E6(40)VE3' is consequence of the endogenous presence of free radicals.

Example 6

Construction of Plasmid VE-TK-pcDNA3 Containing the TK Gene Instead of the Luciferase Reporter Gene and Assays of the In Vitro Antitumor Capacity The plasmid VE-TK-pcDNA3 was obtained through the cloning of the TK insert (SEQ ID NO 23) in sites HindIII and XbaI of the plasmid VE-LUC-pmCMV therefore replacing the luciferase gene for the suicidal gene TK. In this way, the plasmid VE-TK-pmCMV was generated. From the latter, the fragment NotI-VE-TK-XbaI was obtained through the cleavage in the sites NotI and XbaI and it was cloned in the same sites of the pcDNA3 plasmid, obtaining the plasmid VE-TK-pcDNA3. The CMV promoter was previously eliminated from pcDNA3 through a cleavage in the sites BglII and BamHI and then relinked.

Figure 5:
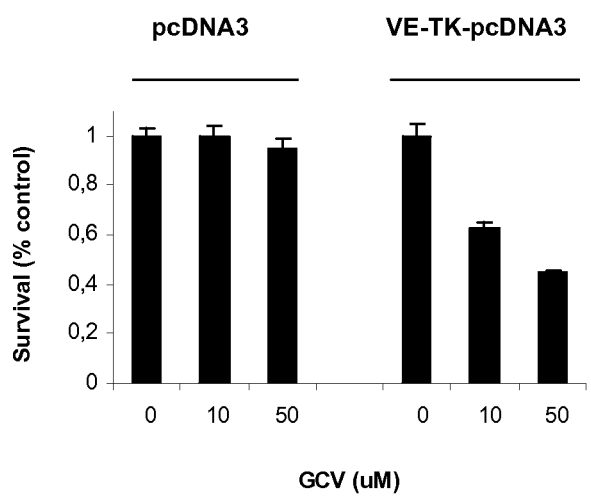
FIG. 5 (a) shows the antitumor activity exerted by VE-TK-pcDNA3 in LoVo cells transiently transfected in the presence of two concentrations of GCV (10 and 50 µM), evaluated through the MTT test and (b) compared the antitumor activity of VE-TK-pcDNA3 with CMV-TK-pcDNA3 in LoVo cells transiently transfected in the presence of GCV (10 and 50 µM) evaluated through the MTT test.
Figure 5:
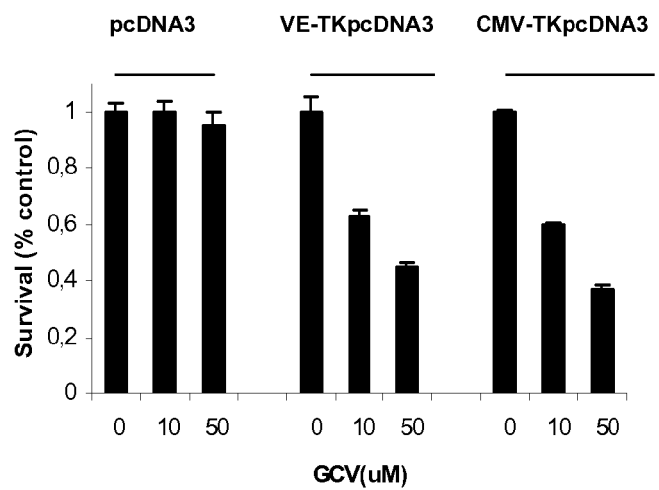

Colorectal LoVo cancer cells were seeded in 24-well plates and transiently transfected with the plasmid VE-TK-pcDNA3 (1.8 µg/well) or with the pcDNA3 empty plasmid. 24 hours later, the cells were treated with trypsin, reseeded in a 1/8 dilution and treated with GCV (10 and 500 µM of GCV, with a change 48 hours later). The survival was expressed in relation with the cells not exposed to the GCV. The survival was evaluated by the MTT assay, as detailed before. The VE motif or element in this case was capable of driving the TK therapeutic gene expression. The results of this assay, in the presence of the two concentrations of GCV used, are shown in FIG. 5 (a).

Also, the activity of the VE-TK-pcDNA3 was compared with that of the pcDNA3 plasmid expressing TK. As can be seen in FIG. 5 (b), the same level of antitumor activity was obtained in the presence of GCV, for VE as well as for CMV. The effect of the VE element alone, in vitro, over tumor cells, shows that its activity is as powerful as that of the CMV promoter, proving how strong it is.

Example 7

Construction of a Plasmid Containing 5'E6(40)VE3' Upstream of Suicidal Gene hsv-TK and In Vitro and In Vivo Assays of the Antitumor Capacity In Vitro Studies In order to evaluate if 5'E6(40)VE3' may drive the expression of a therapeutic gene, the luciferase cDNA was replaced by the thymidine kinase gene (TK) of the simplex herpes virus (SEQ ID NO. 23), obtaining the vector E6(40)VE-TK. To this effect, a fragment HindIII-TK-SalI was cloned downstream of the promoter 5'E6(40)VE3' of plasmid E6(40)VE-LUC in the sites HindIII and SalI; this way, the luciferase cDNA was replaced by the hsv-TK gene. This result was confirmed through sequencing using the universal primers T3 (ATTAACCCTCATAAAGGGA) (SEQ ID NO. 26) and T2 (CTTTATGTTTTTGGCGTCTTCCA) (SEQ ID NO. 27).

Figure 6:
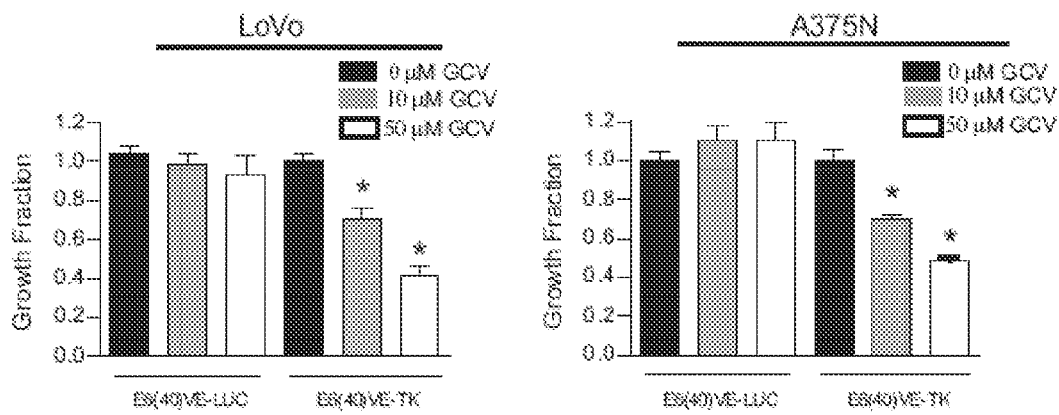
FIG. 6 shows: (a) an MTT assay of transiently transfected cells with E6(40)VE-TK in the A375N and LoVo cell lines in the presence and absence of GCV. As specificity control of the transgene, cells were transfected with E6(40)VE-LUC, Data show the mean±SD values of 3 independent experiments (*P<0.0001). (b) A375N and LoVo cells transfected with E6(40)VE-TK in the presence and absence of GCV were stained with crystal violet. Cells were transfected with E6(40) VE-LUC as control of transgene specificity expression (c) Spheroids made of LoVo or A375N cells transiently transfected with E6(40)VE-LUC or E6(40)VE-TK plasmids in the absence and presence of GCV. Data represent the mean±SD of measurements from 3-8 spheroids, corresponding to one of two independent experiments. (d) In vivo tumorigenicity of LoVo and A375N cells transiently transfected with E6(40) VE-TK in nude mice treated intraperitoneally with PBS or with GCV (50 mg/ml) every day during the first 10 days after inoculation (n=5-7 mice per group); (*P<0.0002 for the melanoma model); photographs taken on day 50.
Figure 6:
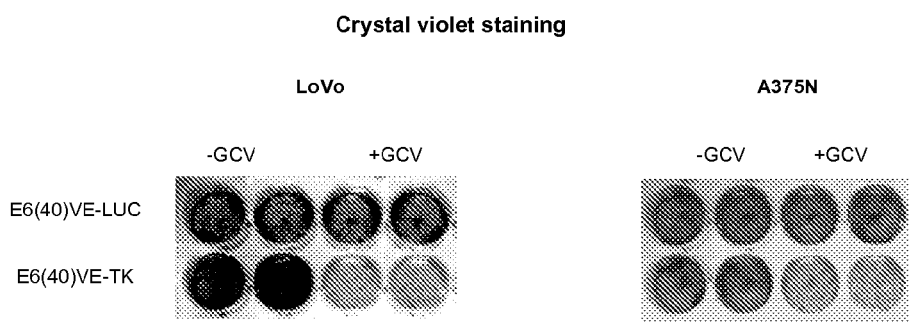
Figure 6:
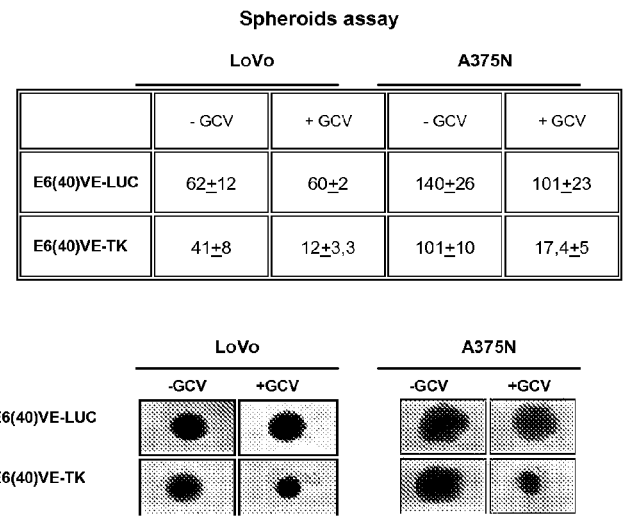
Figure 6:
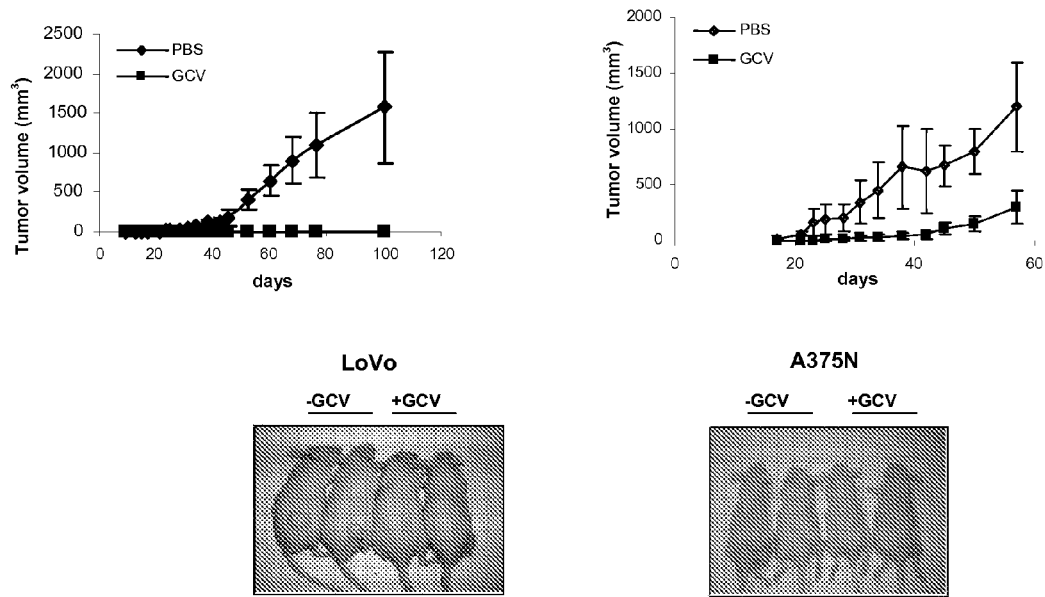

Once the presence of the TK gene was confirmed, its antitumor capacity was evaluated through MTT assays. The MTT assay (cellular viability) is based on the conversion of yellow tetrazolium salt into a purple colored compound (formazan) spectrophotometrically quantifiable to 570 nm. This reaction only occurs in metabolically active cells that have the succinate-tetrazoil reductase enzyme present in the mitochondria breathing chain. The antitumor effect of E6(40)VE-TK measured in relation with the metabolic activity (MTT assay) are shown in FIG. 6 (a) for tumor colon cells (LoVo) and melanoma (A375N).

LoVo and A375N $5 \times 10^4$ cells were seeded in 24-well plates and were transfected with 1.8 µg/well of the plasmid E6(40) VE-TK using Lipofectamina2000. After 24 hours, the cells were treated with trypsine and diluted in 1/6, and, 4 hours later, ganciclovir was added (10 and 50 µM). This means was changed every 48 hours and the proliferation was evaluated through the MTT assay. As transfection and specificity controls, these lines were similarly transfected with E6(40)VE-LUC performing the same procedure. The cells transfected with E6(40)VE-TK and treated with GCV showed a significant growth inhibition as compared to the cells transfected with E6(40)VE-LUC and exposed to GCV (see FIG. 6 (a)).

In addition, the survival was evaluated through the crystal violet staining (0.75% solution in 40% methanol). FIG. 6 (b) shows photographs of the plates of the LoVo and A375N cultures treated with the vectors E6(40)VE-LUC and E6(40) VE-TK, in the assay with crystal violet.

On the other hand, the effect of E6(40)VE-TK/GCV was evaluated on spheroids formed with the technique described by Dangles-Marie (Dangles-Marie, V., et al., *A three-dimensional tumor cell defect in activating autologous CTLs is associated with inefficient antigen presentation correlated with heat shock protein-70 down-regulation.* Cancer Res, 2003. 63(13): p. 3682-7). To this end, LoVo and A375N cells were seeded in 24-well plates and were transiently transfected with 1.8 µg/well of E6(40)VE-TK or E6(40)VE-LUC as a control. After 24 hours, the cells were treated with trypsin and seeded in 96-well plates ($1 \times 10^4$ in means of 100 µl) that were previously covered with 75 µl of agarose 1%. The GCV was added after 24 hours, and were renewed every 72 hours; the greater and smaller diameter of the same were evaluated twice a week. Growth curves were obtained for both cell lines (data not shown). The volume of the spheroids formed by transiently transfected cells with E6(40)VE-TK and treated with GCV differs significantly from the volume of the spheroids transfected with E6(40)VE-TK and not exposed to GCV. FIG. 6 (c) shows the photographs of the prepared spheroids. The results can be seen in the Table below:

|  | LoVo | | A375N | |
| --- | --- | --- | --- | --- |
|  | −GCV | +GCV | −GCV | +GCV |
| E6(40)VE-LUC | 62 ± 12 | 60 ± 2 | 140 ± 26 | 101 ± 23 |
| E6(40)VE-TK | 41 ± 8 | 12 ± 3.3 | 101 ± 10 | 17.4 ± 5 |

There are no effects on the spheroids formed with cells transiently transfected with E6(40)VE-LUC and treated with GCV, proving the specificity of the action of the TK.

In Vivo Studies

The cells A375N and LoVo previously transiently transfected with E6(40)VE-TK were subsequently inoculated in nude mice. Athymic 6-8 weeks old Male animals N:NIH(S) were used (obtained from the biotherium of the National Commission of Atomic Energy (Comisión Nacional de Energia Atómica)). The animals were injected with $2.5 \times 10^6$ of A375N cells or with $4 \times 10^6$ of LoVo cells, previously transfected with E6(40)VE-TK. Subsequently, the animals were treated intraperitoneally (i.p) with GCV (50 mg/kg) during 10 days. The control group received only vehicle, that is, PBS. FIG. 6 (d) shows the tumor growth curves in mice injected with A375N and LoVo cells previously transfected with E6(40)VE-TK. FIG. 6 (d) also shows pictures of mice injected with PBS or GCV intraperitoneally, 50 days after being injected. There is a complete growth inhibition in the animals inoculated with previously transfected LoVo cells, and a strong delay in growth in the animals inoculated with A375N.

Example 8

Combination of E6(40)VE-TK with Ionizing Radiation and with Chemotherapeutic Drugs In Vitro Studies Since on the one hand the promoter has an element responsive to the ionizing radiation, but on the other hand, the ionizing radiation generates free radicals through water radiolysis, the possible additive effect of E6(40)VE-TK was evaluated with ionizing radiation.

Figure 7:
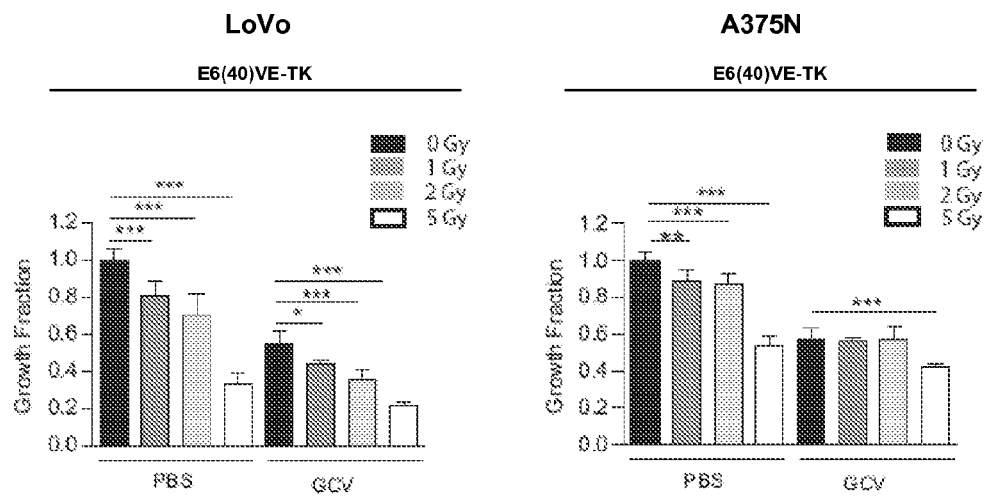
FIG. 7 shows A375N and LoVo transiently transfected with cells E6(40)VE-TK in presence or absence GCV treated or not with GCV in combination with (a) ionizing radiation or (*P<0.001, (P<0.01) (b) chemotherapeutic drugs Dx (0.5 µM), or Bleo (20 µM) and exposed in the presence or absence of 10 µM or 50 µM GCV. Growth inhibition was measured by the MTT assay and "growth fraction" refers to the inhibition seen in comparison with untreated cells (***P<0.001). (c) Spheroids made of LoVo or A375N cells, transiently transfected with E6(40)VE-TK, were exposed to GCV (50 µM), Dx (0.5 µM), or both. Spheroid growth was measured using the MTT assay. Data show the mean±SD of 3-5 measurements within a representative experiment of two experiments. Each measurement includes one spheroid of A375N cells and a pool of three spheroids for LoVo cells. Inset: photomicrographs (25×) of spheroids taken at day 20. (*P<0.05, and **P<0.01). Data show the mean±SD values of 3 independent experiments and lines over the bars indicate the groups that were compared.
Figure 7:
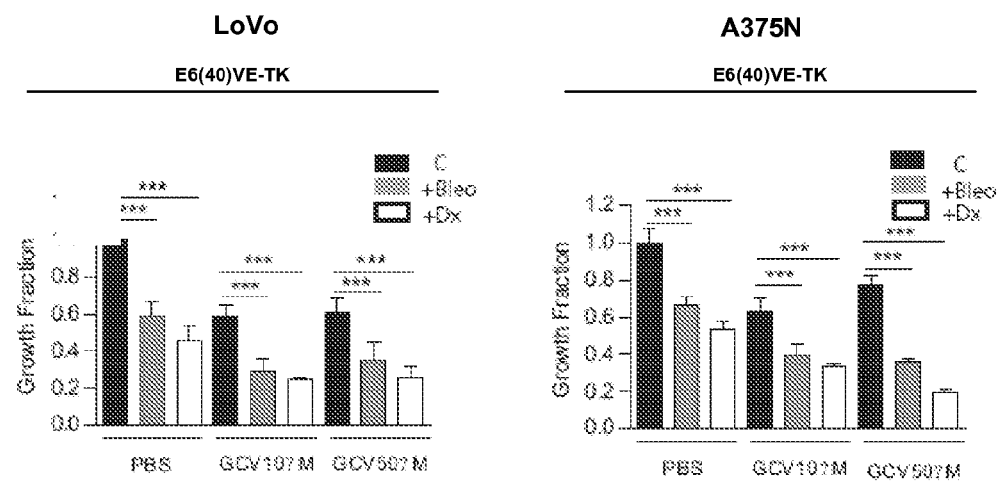
Figure 7:
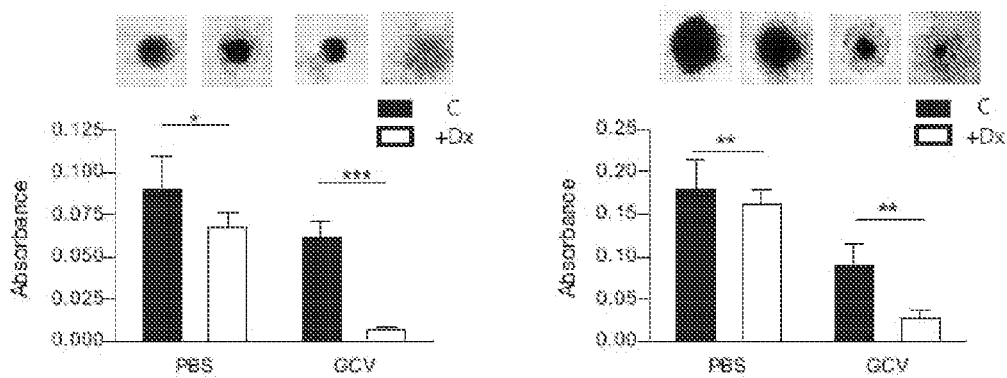

These experiments were made in the same fashion as those described in Example 7, with the addition of gamma radiation and chemotherapeutic drugs. Regarding the combined experiments with gamma radiation, the cells were irradiated with 1, 2 and 5 Gy (gray) 24 hours after the first addition of GCV (10 µM). The results are shown in FIG. 7 (a), for the treated LoVo tumor cells (colon) and A375N (melanoma).

As per chemotherapeutic drugs, doxorubicin (0.5 µM) or bleomycin (20 µM) was added 48 hours after the first addition of GCV (10 µM). In both cases, an additive effect was observed in both treatments in the two assayed cell lines. The results are shown in FIG. 7 (b).

The combination of treatments was also made in spheroids. In this case, doxorubicin (0.5 µM) was added 4 days after seeding. The effect of the treatments was measured through the MTT technique 10 days after the beginning of the treatment. For this, the spheroids were incubated with 0.5 mg/ml of MTT during 2 hours, after which the spheroids were absorbed and gathered. The spheroids were centrifuged 2 minutes at 14000 rpm, the supernatant was discarded and they were suspended again in 50 µl of DMSO, evaluating the absorbance at 590 nm. The survival was expressed as % of the control (spheroids not treated with GCV).

In this case there was also an additive effect in both treatments. FIG. 7 (c) shows photographs of prepared spheroids.

Example 9

Effect of E6(40)VE-TK in Established Tumors and Combination with Doxorubicin

In Vivo Studies

The antitumor capacity of E6(40)VE-TK was evaluated in established tumors. Since the entry of a naked plasmid into an in vivo cell is a very inefficient process, it was decided to make use of electrotransference techniques. This technique consists in applying an electric pulse, which has proved to generate transitory pores in the membrane of the cells allowing the entrance of the plasmid (Heller LC, Ugen K, Heller R, *Electroporation for targeted gene transfer. Expert Opin Drug Deliv.* 2005, 2:255-68). This technique is being used at present in patients in clinical protocols for optimizing the entrance of chemotherapeutic drugs in the treatment of melanoma (Giardino R, Fini M, Bonazzi V, Cadossi R, Nicolini A, Carpi A. *Electrochemotherapy a novel approach to the treatment of metastatic nodules on the skin and subcutaneous tissues. Biomed Pharmacother.* 2006 September; 60(8):458-62).

Athymic 6-8 weeks old male animals were used. The animals were injected with $2.5 \times 10^6$ A375N cells and with $4 \times 10^6$ LoVo cells. When the tumors reached an average size of between 100-200 $mm^3$ (approximately after 20 days), the intratumoral treatment started with the plasmid E6(40)VE-TK. The animals were divided in four experimental groups containing 5 animals per group. The groups were: E6(40)VE-TK/PBS, shown in FIG. 8 (a); E6(40)VE-TK/PBS/Dx, shown in FIG. 8 (b); E6(40)VE-TK/GCV, shown in FIG. 8 (c); and E6(40)VE-TK/GCV/Dx, shown in FIG. 8 (d).

Prior to the administration of the plasmid, the animals were anesthetized with xylacine and ketamine. The plasmid was injected intratumorally (50 µg ADN/in 100 µl of PBS) in all the animals. Approximately within the consecutive minute to the local administration of the plasmid, 6 pulses of 20 ms were applied with a voltage of 400 mV/cm with an electrode having 0.5 cm spacing. 6 applications of E6(40)VE-TK were administered on days 1, 3, 5, 7, 9 and 11. Half the animals were administered with i.p. GCV (50 mg/kg), starting on day 1 and during 15 consecutive days. As control, the tumors were injected the same way but they were administered intraperitoneal (i.p.). PBS For the experiments combining E6(40)VE-TK/GCV with doxorubicin, a dose of 5 mg/kg i.p. of doxorubicin was applied on days 3, 7 and 11 to half the animals treated with E6(40)VE-TK/GCV, and also to half the animals treated with E6(40)VE-TK/i.p. PBS.

Figure 8:
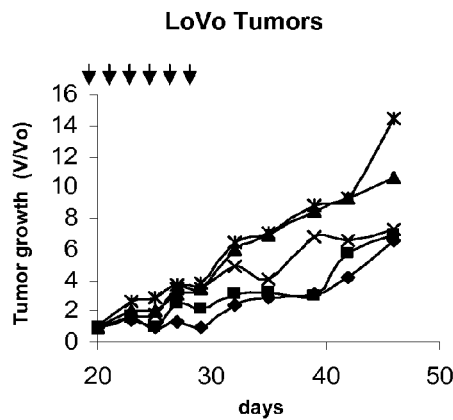
FIG. 8 shows established tumor growth curves of LoVo and A375N treated intratumorally with E6(40)VE-TK administered by electrotransference; the animals were treated with (a) ip PBS; (b) ip PBS and Dx; (c) ip GCV; and (d) ip GCV and Dx; the plasmid was administered in 6 applications of 50 µg DNA/100 µl per tumor with 6 pulses of 20 ms of 400V/cm on days 1, 3, 5, 7, 9 and 11. Doxorubicin (5 mg/kg) was administered intraperitoneally on days 3, 7 and 11; the GCV (50 mg/kg) or i.p. PBS daily during 12 days; (e) photograph of A375N tumors treated with E6(40)VE-TK with PBS, DX, GCV and GCV+DX.
Figure 8:
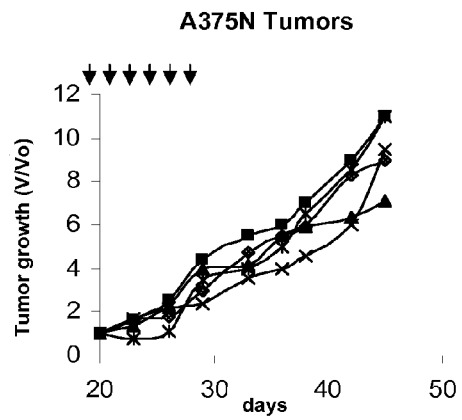
Figure 8:
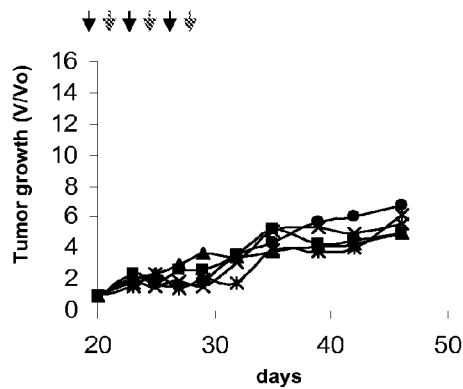
Figure 8:
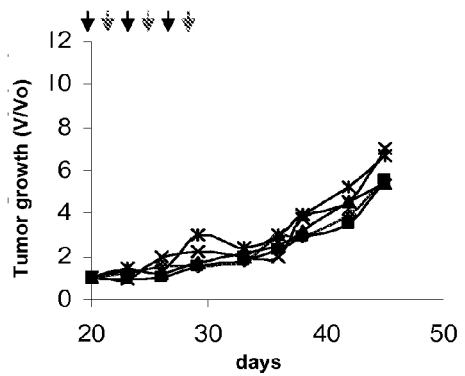
Figure 8:
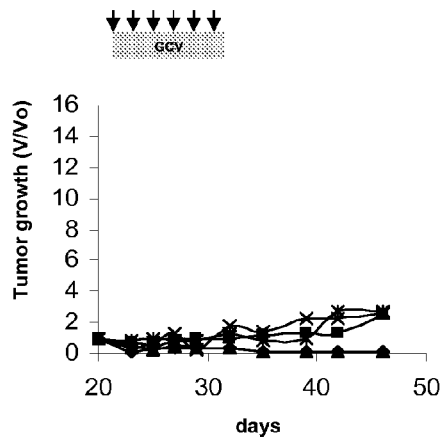
Figure 8:
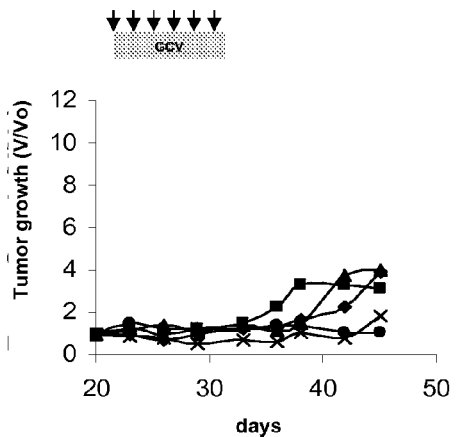
Figure 8:
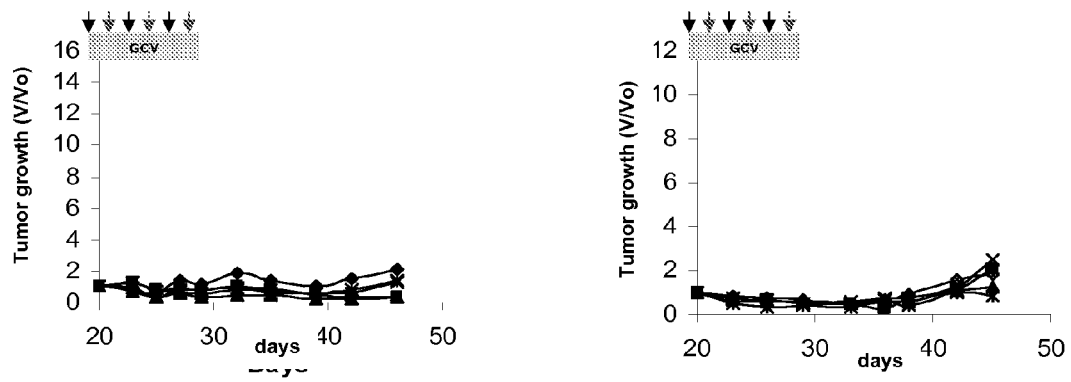
Figure 8:
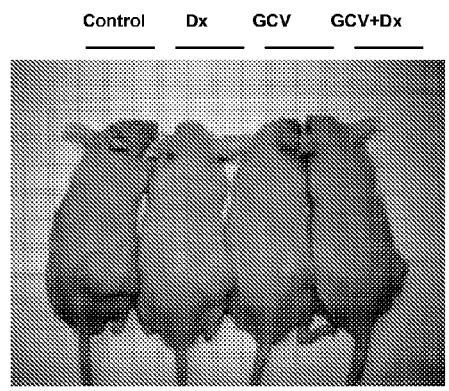

As can be seen in FIGS. 8 (a) to (e), the mice treated with GCV inhibited strongly its growth. On the other hand, and additive effect was observed in mice treated with E6(40)VE-TK/GCV/Dx.

The changes and variations of the examples described in the invention will be evident for the experts in the art, without departing from the scope and spirit of the same. Even though the invention has been described respect of specific embodiments, the invention should be understood according to what is claimed, and should not be limited to said specific embodiments. In fact, several changes of the ways described to perform the invention, which are obvious to those skilled in the art, are conceived as within the scope of the following claims.

The invention claimed is:

1. A promoter inducible by reactive oxygen species (ROS), the promoter consisting of a chimeric promoter containing an E6 element consisting of the nucleotide sequence of SEQ ID NO: 2 spaced from a VE element consisting of the nucleotide sequence of SEQ ID NO: 1 by a spacing sequence.

2. The promoter according to claim 1, wherein the spacing sequence is between 6 and 200 base pairs.

3. The promoter according to claim 2, wherein the spacing sequence is selected from the group of 6 base pairs, 20 base pairs and 40 base pairs.

4. The promoter according to claim 2, wherein the chimeric promoter is 5'E6(40)VE3' consisting of the nucleotide sequence of SEQ ID NO:12.

5. A vector comprising a promoter inducible by reactive oxygen species (ROS), the vector consisting of a chimeric promoter containing an E6 element consisting of the nucleotide sequence of SEQ ID NO: 2 spaced from a VE element consisting of the nucleotide sequence of SEQ ID NO: 1 by a spacing sequence.

6. The vector according to claim 5, wherein the spacing sequence is between 6 and 200 base pairs.

7. The vector according to claim 6, wherein the spacing sequence is selected from the group of 6 base pairs, 20 base pairs and 40 base pairs.

8. The vector according to claim 6, wherein the chimeric promoter is 5'E6(40)VE3' consisting of the nucleotide sequence of SEQ ID NO: 12.

9. The vector according to claim 8, further comprising a therapeutic human gene operatively linked to said promoter sequence.

10. The vector according to claim 5, further comprising a gene of interest, operatively linked to said promoter sequence.

11. The vector according to claim 10, wherein the gene of interest is a therapeutic human gene.

12. The vector according to claim 11, wherein the therapeutic human gene is a suicidal gene.

13. The vector according to claim 10, wherein the gene encodes a protein detectable in vivo.

14. The vector according to claim 5, wherein the vector is selected from a viral and a non-viral vector.

15. A pharmaceutical composition comprising a vector according to claim 5 in a pharmaceutically acceptable carrier.

16. The composition according to claim 15, further comprising a chemotherapeutical drug.

17. The pharmaceutical composition according to claim 15, wherein the carrier is a cell.

* * * * *

SEQUENCE LISTING

<160> NUMBER OF SEQ ID NOS: 29

<210> SEQ ID NO 1
<211> LENGTH: 36
<212> TYPE: DNA
<213> ORGANISM: Artificial Sequence
<220> FEATURE:
<223> OTHER INFORMATION: Promoter sequence derived from the VEGF promoter

```
<400> SEQUENCE: 1
ggggcgggcc gggggcgggg tcccggcggg gcggag                                36

<210> SEQ ID NO 2
<211> LENGTH: 60
<212> TYPE: DNA
<213> ORGANISM: Artificial Sequence
<220> FEATURE:
<223> OTHER INFORMATION: Promoter sequence derived from the EGR-1
      promoter

<400> SEQUENCE: 2
ccatataagg ccatataagg ccatataagg ccatataagg ccatataagg ccatataagg      60

<210> SEQ ID NO 3
<211> LENGTH: 532
<212> TYPE: DNA
<213> ORGANISM: Artificial Sequence
<220> FEATURE:
<223> OTHER INFORMATION: Promoter sequence derived from the MMP-1
      promoter

<400> SEQUENCE: 3
agtgtatgag actcttccag ggtgacgtct taggcaattt cctgtccaat cacagatggt      60
cacatgctgc tttcctgagt taacctatta actcacccct gtttcccagg cctcagtgga     120
gctaggcttg tcacgtcttc acagtgacta gattccctca cagtcgagta tatctgccac     180
tccttgactt ttaaaacata gtctatgttc accctctaat atgaagagcc cctttcacta     240
ttttctttgt ctgtgctgga gtcacttcag tggcaagtgt tctttggtct ctgccgcacc     300
ctccctctga tgcctctgag aagaggattt ccttttcgtg agaatgtctt cccattcttc     360
ttaccctctt gaactcacat gttatgccac ttagatgagg aaattgtagt taaataatta     420
gaaagatatg acttatctca aatcaatcca agatatactg aagtattgtt tatgagtaag     480
atatcagtct tgacgcagaa agaaaacagg aatccataag gggaggaaag tg             532

<210> SEQ ID NO 4
<211> LENGTH: 40
<212> TYPE: DNA
<213> ORGANISM: Artificial Sequence
<220> FEATURE:
<223> OTHER INFORMATION: Synthetic oligonucleotide corresponding to the
      promoter sequence derived from the VEGF promoter (oligo 1 VEGF)

<400> SEQUENCE: 4
cggggcgggc cggggggcggg cggggtccgg cgggcggaga                           40

<210> SEQ ID NO 5
<211> LENGTH: 46
<212> TYPE: DNA
<213> ORGANISM: Artificial Sequence
<220> FEATURE:
<223> OTHER INFORMATION: Synthetic oligonucleotide corresponding to the
      promoter sequence derived from the VEGF promoter (oligo 2 VEGF)

<400> SEQUENCE: 5
cgcgtctccg ccccgccggg accccgcccc cggcccgccc cggtac                     46

<210> SEQ ID NO 6
<211> LENGTH: 66
<212> TYPE: DNA
<213> ORGANISM: Artificial Sequence
<220> FEATURE:
<223> OTHER INFORMATION: Synthetic oligonucleotide corresponding to the
      promoter sequence derived from the E6 promoter (oligo 1 E6)
```

-continued

```
<400> SEQUENCE: 6
cgcgtccata taaggccata taaggccata taaggccata taaggccata taaggccata    60
taaggc                                                                66

<210> SEQ ID NO 7
<211> LENGTH: 66
<212> TYPE: DNA
<213> ORGANISM: Artificial Sequence
<220> FEATURE:
<223> OTHER INFORMATION: Synthetic oligonucleotide corresponding to the
      promoter sequence derived from the E6 promoter (oligo 2 E6)

<400> SEQUENCE: 7
tcgagcctta tatggcctta tatggcctta tatggcctta tatggcctta tatggcctta    60
tatgga                                                                66

<210> SEQ ID NO 8
<211> LENGTH: 33
<212> TYPE: DNA
<213> ORGANISM: Artificial Sequence
<220> FEATURE:
<223> OTHER INFORMATION: Primer (oligo 1 MMP-1)

<400> SEQUENCE: 8
cggggtacca cagtgtatga gactcttcca ggg                                  33

<210> SEQ ID NO 9
<211> LENGTH: 39
<212> TYPE: DNA
<213> ORGANISM: Artificial Sequence
<220> FEATURE:
<223> OTHER INFORMATION: Primer (oligo 2 MMP-1)

<400> SEQUENCE: 9
cgacgcgtca ctttcctccc ctccccttat ggattcctg                            39

<210> SEQ ID NO 10
<211> LENGTH: 102
<212> TYPE: DNA
<213> ORGANISM: Artificial Sequence
<220> FEATURE:
<223> OTHER INFORMATION: Promoter sequence derived from the promoter of
      E6 and VE (E6 (6) VE)

<400> SEQUENCE: 10
ccatataagg ccatataagg ccatataagg ccatataagg ccatataagg ccatataagg    60
acgcgtgggg cgggccgggg gcgggtcccc ggcggggcgg ag                       102

<210> SEQ ID NO 11
<211> LENGTH: 102
<212> TYPE: DNA
<213> ORGANISM: Artificial Sequence
<220> FEATURE:
<223> OTHER INFORMATION: Promoter sequence derived from the promoter of
      VE and E6 (VE (6) E6)

<400> SEQUENCE: 11
ggggcgggcc ggggcgggg tcccggcggg gcggagacgc gtccatataa ggccatataa    60
ggccatataa ggccatataa ggccatataa ggccatataa gg                      102

<210> SEQ ID NO 12
<211> LENGTH: 135
<212> TYPE: DNA
```

-continued

```
<213> ORGANISM: Artificial Sequence
<220> FEATURE:
<223> OTHER INFORMATION: Promoter sequence derived from the promoter of
      E6 and VE with a spacing sequence (E6 (40) VE)

<400> SEQUENCE: 12
ccatataagg ccatataagg ccatataagg ccatataagg ccatataagg ccgtataagg     60
acgcgtttgc tagcatcgat tcatatgtac tagtacgcgt gggccgggcc ggggggcgggg   120 tcccggcggg gcgga                                                     135

<210> SEQ ID NO 13
<211> LENGTH: 62
<212> TYPE: DNA
<213> ORGANISM: Artificial Sequence
<220> FEATURE:
<223> OTHER INFORMATION: Synthetic oligonucleotide corresponding to the
      promoter sequence derived from the E6 promoter (oligonucleotide
      E6 3)

<400> SEQUENCE: 13
cccatataag gccatataag gccatataag gccatataag gccatataag gccatataag     60
ga                                                                    62

<210> SEQ ID NO 14
<211> LENGTH: 70
<212> TYPE: DNA
<213> ORGANISM: Artificial Sequence
<220> FEATURE:
<223> OTHER INFORMATION: Synthetic oligonucleotide corresponding to the
      promoter sequence derived from the E6 promoter (oligonucleotide
      E6 4)

<400> SEQUENCE: 14
cgcgtcctta tatggcctta tatggcctta tatggcctta tatggcctta tatggcctta     60
tatggggtac                                                            70

<210> SEQ ID NO 15
<211> LENGTH: 42
<212> TYPE: DNA
<213> ORGANISM: Artificial Sequence
<220> FEATURE:
<223> OTHER INFORMATION: Synthetic oligonucleotide corresponding to the
      promoter sequence derived from the VE promoter (oligonucleotide
      VE 3)

<400> SEQUENCE: 15
cgcgtggggc gggccggggg cggggtcccg gcggggcgga gc                        42

<210> SEQ ID NO 16
<211> LENGTH: 42
<212> TYPE: DNA
<213> ORGANISM: Artificial Sequence
<220> FEATURE:
<223> OTHER INFORMATION: Synthetic oligonucleotide corresponding to the
      promoter sequence derived from the VE promoter (oligonucleotide
      VE 4)

<400> SEQUENCE: 16
tcgagctccg ccccgccggg accccgcccc cggcccgccc ca                        42

<210> SEQ ID NO 17
<211> LENGTH: 41
<212> TYPE: DNA
<213> ORGANISM: Artificial Sequence
<220> FEATURE:
<223> OTHER INFORMATION: Synthetic oligonucleotide corresponding to a
``` spacing sequence (oligonucleotide S1)

<400> SEQUENCE: 17
cgcgtacctc ttagtacata tgaatcgatg ctagtagcaa a     41

<210> SEQ ID NO 18
<211> LENGTH: 34
<212> TYPE: DNA
<213> ORGANISM: Artificial Sequence
<220> FEATURE:
<223> OTHER INFORMATION: Synthetic oligonucleotide corresponding to a
      spacing sequence (oligonucleotide S2)

<400> SEQUENCE: 18
cgcgtttgct agcatcgatt catatgtact agta     34

<210> SEQ ID NO 19
<211> LENGTH: 465
<212> TYPE: DNA
<213> ORGANISM: Homo sapiens
<220> FEATURE:
<221> NAME/KEY: gene
<222> LOCATION: (1)..(465)
<223> OTHER INFORMATION: Sequence corresponding to cDNA of the
      superoxide dismutase depending from Cu and Zn

<400> SEQUENCE: 19
atggcgacga aggccgtgtg cgtgctgaag ggcgacggcc cagtgcaggg catcatcaat     60
ttcgagcaga aggaaagtaa tggaccagtg aaggtgtggg gaagcattaa aggactgact     120
gaaggcctgc atggattcca tgttcatgag tttggagata atacagcagg ctgtaccagt     180
gcaggtcctc actttaatcc tctatccaga aacacggtg gccaaagga tgaagagagg      240 catgttggag acttgggcaa tgtgactgct gacaaagatg gtgtggccga tgtgtctatt     300
gaagattctg tgatctcact ctcaggagac cattgcatca ttggccgcac actggtggtc     360
catgaaaaag cagatgactt gggcaaaggt ggaaatgaag aaagtacaaa gacaggaaac     420
gctggaagtc gtttggcttg tggtgtaatt gggatcgccc aataa     465

<210> SEQ ID NO 20
<211> LENGTH: 21
<212> TYPE: DNA
<213> ORGANISM: Artificial Sequence
<220> FEATURE:
<223> OTHER INFORMATION: Primer 1 SOD1

<400> SEQUENCE: 20
aagcttatgg cgacaaggcc g     21

<210> SEQ ID NO 21
<211> LENGTH: 21
<212> TYPE: DNA
<213> ORGANISM: Artificial Sequence
<220> FEATURE:
<223> OTHER INFORMATION: Primer 2 SOD

<400> SEQUENCE: 21
tctagattat tgggcgatcc c     21

<210> SEQ ID NO 22
<211> LENGTH: 1583
<212> TYPE: DNA
<213> ORGANISM: Homo sapiens
<220> FEATURE:
<221> NAME/KEY: gene
<222> LOCATION: (1)..(1583)

<223> OTHER INFORMATION: Homo sapiens human catalase cDNA

<400> SEQUENCE: 22

```
atggctgaca gccgggatcc cgccagcgac cagatgcagc actggaagga gcagcgggcc      60
gcgcagaaag ctgatgtcct gaccactgga gctggtaacc cagtaggaga caaacttaat     120
gttattacag tagggccccg tgggccccct tcttgttcagg atgtggtttt cactgatgaa     180
atggctcatt tgaccgaga gagaattcct gagagagttg tgcatgctaa aggagcaggg      240
gcctttggct actttgaggt cacacatgac attaccaaat actccaaggc aaaggtattt     300
gagcatattg gaagaagac tcccatcgca gttcggttct ccactgttgc tggagaatcg      360
ggttcagctg acacagttcg ggaccctcgt gggtttgcag tgaaatttta cacagaagat     420
ggtaactggg atctcgttgg aaataacacc cccattttct tcatcaggga tcccatattg     480
tttccatctt ttatccacag ccaaaagaga aatcctcaga cacatctgaa ggatccggac     540
atggtctggg acttctggag cctacgtcct gagtctctgc atcaggtttc tttcttgttc     600
agtgatcggg ggattccaga tggacatcgc cacatgaatg gatatggatc acatactttc     660
aagctggtta atgcaaatgg ggaggcagtt attgcaaatt ccattataag actgaccagg     720
gcatcaaaaa cctttctgtt gaagatgcgg cgagactttc ccaggaagat cctgactatg     780
gcatccggga tcttttaac gccattgcca caggaaagta cccctcctgg acttttaca      840
tccaggtcat gacatttaat caggcagaaa cttttccatt taatccattc gatctcacca     900
aggtttggcc tcacaaggac taccctctca tcccagttgg taaactggtc ttaaaccgga     960
atccagttaa ttactttgct gaggttgaac agatagcctt cgacccaagc aacatgccac    1020
ctggcattga ggccagtcct gacaaaatgc ttcagggccg ccttttttgcc tatcctgaca    1080
ctcaccgcca tcgcctggga cccaattatc ttcatatacc tgtgaactgt ccctaccgtg    1140
ctcgagtggc caactaccag cgtgacggcc cgatgtgcat gcaggacaat cagggtggtg    1200
ctccaaatta ctaccccaac agctttggtg ctccggaaca cagccttct gccctggagc    1260
acagcatcca atattctgga gaagtgcgga gattcaacac tgccaatgat gataacgtta    1320
ctcaggtgcg ggcattctat gtgaacgtgc tgaatgagga acagaggaaa cgtctgtgtg    1380
agaacattgc cggccacctg aaggatgcac aaattttcat ccagaagaaa gcggtcaaga    1440
acttcactga ggtccaccct gactacggga gccacatcca ggctcttctg gacaagtaca    1500
atgctgagaa gcctaagaat gcgattcaca ctttgtgca gtccggatct cacttggcgg    1560
caagggagaa ggcaaatctg tga                                            1583
```

<210> SEQ ID NO 23
<211> LENGTH: 1039
<212> TYPE: DNA
<213> ORGANISM: type 1 Herpes simplex virus
<220> FEATURE:
<221> NAME/KEY: gene
<222> LOCATION: (1)..(1039)
<223> OTHER INFORMATION: Thymidine Kinase cDNA

<400> SEQUENCE: 23

```
atggcttcgt accctgcca tcaacacgcg tctgcgttcg accaggctgc gcgttctcgc      60
ggccatagca accgacgtac ggcgttgcgc cctcgccggc agcaagaagc cacggaagtc     120
cgcccggagc agaaaatgcc cacgctactg cgggtttata tagacggtcc ccacgggatg     180
gggaaaacca ccaccacgca actgctggtg gccctgggtt cgcgcgacga tatcgtctac     240
gtacccgagc cgatgactta ctggcgggtg ctgggggctt ccgagacaat cgcgaacatc     300
```

| | |
|---|---|
| tacaccacac aacaccgcct cgaccagggt gagatatcgc cggggacgcg gcggtggtaa | 360 |
| tgacaagcgc ccagataaca atgggcatgc cttatgccgt gaccgacgcc gttctggctc | 420 |
| ctcatatcgg gggggaggct gggagctcac atgccccgcc cccggccctc accctcatct | 480 |
| tcgaccgcca tcccatcgcc gccctcctgt gctaccggc cgcgcggtac cttatgggca | 540 |
| gcatgacccc ccaggccgtg ctggcgttcg tggccctcat cccgccgacc ttgcccggca | 600 |
| caaacatcgt gttggggggcc cttccggagg acagacacat cgaccgcctg gccaaacgcc | 660 |
| agcgccccgg tgagcggctt gacctggcta tgctggccgc gattcgccgc gtttacgggc | 720 |
| tacttgccaa tacggtgcgg tatctgcagt gcggcgggtc gtggcgggag gattggggac | 780 |
| agctttcggg gacggccttg acgccccagg gtgccgagcc ccagagcaac gcgggcccac | 840 |
| gaccccatat cggggaaacg ttatttaccc tgtttcgggc ccccgagttg ctggcccca | 900 |
| acggcgacct gtacaacgtg tttgcctggg ccttggacgt cttggccaaa cgcctccgtc | 960 |
| ccatgcacgt ctttatcctg gattacgacc aatcgcccgc cggctgccgg gacgccctgc | 1020 |
| tgcaacttac ctccgggat | 1039 |

<210> SEQ ID NO 24
<211> LENGTH: 21
<212> TYPE: DNA
<213> ORGANISM: Artificial Sequence
<220> FEATURE:
<223> OTHER INFORMATION: Primer P3

<400> SEQUENCE: 24

| | |
|---|---|
| ctagcaaaat aggctgtccc c | 21 |

<210> SEQ ID NO 25
<211> LENGTH: 23
<212> TYPE: DNA
<213> ORGANISM: Artificial Sequence
<220> FEATURE:
<223> OTHER INFORMATION: Primer P2

<400> SEQUENCE: 25

| | |
|---|---|
| ctttatgttt ttggcgtctt cca | 23 |

<210> SEQ ID NO 26
<211> LENGTH: 19
<212> TYPE: DNA
<213> ORGANISM: Artificial Sequence
<220> FEATURE:
<223> OTHER INFORMATION: Primer T3

<400> SEQUENCE: 26

| | |
|---|---|
| attaaccctc ataaggga | 19 |

<210> SEQ ID NO 27
<211> LENGTH: 23
<212> TYPE: DNA
<213> ORGANISM: Artificial Sequence
<220> FEATURE:
<223> OTHER INFORMATION: Primer T2

<400> SEQUENCE: 27

| | |
|---|---|
| ctttatgttt ttggcgtctt cca | 23 |

<210> SEQ ID NO 28
<211> LENGTH: 40
<212> TYPE: DNA
<213> ORGANISM: Artificial Sequence
<220> FEATURE:

```
<223> OTHER INFORMATION: Spacing sequence

<400> SEQUENCE: 28
acgcgtttgc tagcatcgat tcatatgtac tagtacgcgt                              40

<210> SEQ ID NO 29
<211> LENGTH: 10
<212> TYPE: DNA
<213> ORGANISM: Artificial Sequence
<220> FEATURE:
<223> OTHER INFORMATION: CArG domain
<220> FEATURE:
<221> NAME/KEY: misc_feature
<222> LOCATION: (3)..(8)
<223> OTHER INFORMATION: n is a or t

<400> SEQUENCE: 29 ccnnnnnngg                                                               10
```